US012624357B2

(12) United States Patent
Kim et al.

(10) Patent No.: US 12,624,357 B2
(45) Date of Patent: May 12, 2026

(54) METHODS AND COMPOSITIONS TO PROMOTING RETINAL REGENERATION USING PROX1 MIGRATION INHIBITOR AS ACTIVE INGREDIENT

(71) Applicant: KOREA ADVANCED INSTITUTE OF SCIENCE AND TECHNOLOGY, Daejeon (KR)

(72) Inventors: Jin Woo Kim, Daejeon (KR); Eun Jung Lee, Daejeon (KR)

(73) Assignee: KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 955 days.

(21) Appl. No.: 17/842,610

(22) Filed: Jun. 16, 2022

(65) Prior Publication Data

US 2023/0029377 A1    Jan. 26, 2023

Related U.S. Application Data

(63) Continuation of application No. PCT/KR2021/008044, filed on Jun. 25, 2021.

(30) Foreign Application Priority Data

Jun. 25, 2020   (KR) ........................ 10-2020-0078016
Jun. 14, 2021   (KR) ........................ 10-2021-0077060

(51) Int. Cl.
*C12N 15/113* (2010.01)
*A61P 27/02* (2006.01)
*C12N 9/22* (2006.01)
*C12N 15/11* (2006.01)

(52) U.S. Cl.
CPC .......... *C12N 15/1138* (2013.01); *A61P 27/02* (2018.01); *C12N 9/22* (2013.01); *C12N 15/11* (2013.01); *C12N 2310/12* (2013.01); *C12N 2310/14* (2013.01); *C12N 2310/531* (2013.01)

(58) Field of Classification Search
None
See application file for complete search history.

(56) References Cited

U.S. PATENT DOCUMENTS

| | | | |
|---|---|---|---|
| 2003/0224516 A1 | 12/2003 | Dobie | |
| 2007/0048313 A1* | 3/2007 | Duncan ................. | C07K 16/18 435/7.1 |
| 2021/0228741 A1 | 7/2021 | Reh et al. | |
| 2023/0250424 A1* | 8/2023 | Jung .................... | G01N 33/574 514/44 A |

FOREIGN PATENT DOCUMENTS

| | | | |
|---|---|---|---|
| KR | 10-2011-0117982 A | 10/2011 | |
| KR | 10-2015-0035432 A | 4/2015 | |
| KR | 10-2019-0037166 A | 4/2019 | |
| KR | 2099335 B1 * | 4/2020 | ........... A61K 39/395 |

OTHER PUBLICATIONS

Chen, Xiaoren; et al; "Production of Monoclonal Antibodies Against Prox1" Hybridoma, 25, 27-33, 2006 (Year: 2006).*
International Search Report and Written Opinion issued for corresponding PCT Patent Application No. PCT/KR2021/008044 dated Oct. 25, 2021.
NCBI, Gen Bank Accession No. BC024201.2, *Homo sapiens* prospero homeobox 1, mRNA (cDNA clone MGC:3668 Image:3532312), complete cds, Sep. 11, 2007.
Japanese Office Action, issued May 16, 2023, for corresponding JP 2022-537771.
Jimmy De Melo et al., "Injury-independent induction of reactive gliosis in retina by loss of function of the LIM homeodomain transcription factor Lhx2" PNAS Mar. 20,2012, vol. 109, No. 12.
Neurorehabilitation and Neural Repair, 2009, vol. 23, No. 9, p. 960 O-9.
Elena Cid et al., "Prox1 expression in rod precursors and Müller cells" Experimental Eye Research 90 (2010) 267e276.
Michael A. Dyer et al., "Prox1 function controls progenitor cell proliferation and horizontal cell genesis in the mammalian retina", 2003 Nature Publishing Group.
Nikolas L. Jorstad et al., "Stimulation of functional neuronal regeneration from Müller glia in adult mice" Aug. 3, 2017, vol. 548, Nature, 103.
Chinese Office Action, issued Aug. 12, 2023 for corresponding CN 202180007835.8, pp. 1-8.
Thanh Hoang et al., "Gene regulatory networks controlling vertebrate retinal regeneration", Science 370(2020).
Korean Office Action, issued Aug. 16, 2023, pp. 1-5.
Strausberg,R.L., "*Homo sapiens* prospero homeobox 1, mRNA (cDNA clone MGC:3668 Image:3532312)", complete cds, BC024201.2, NCBI GenBank, dated Sep. 11, 2007.

* cited by examiner

*Primary Examiner* — David W Berke-Schlessel
(74) *Attorney, Agent, or Firm* — Tarolli, Sundheim, Covell & Tummino LLP

(57) ABSTRACT

The present invention relates to a technique capable of treating a retinal neurodegenerative disease through regeneration of a retinal nerve by targeting Prox1 in the mammalian retina using an inhibitor which inhibits Prox1 expression or migration. According to the present invention, inducing the regeneration of the damaged retina in mammals, and thus can be commonly applied to the treatment of various retinal neurodegenerative diseases causing vision loss, and furthermore, when combining with a selective retinal nerve differentiation method or the like, it is expected that the method can be used for the development of an innovative retinal regeneration method capable of selectively regenerating only specific degenerating retinal neurons.

7 Claims, 15 Drawing Sheets

Specification includes a Sequence Listing.

FIG 1B
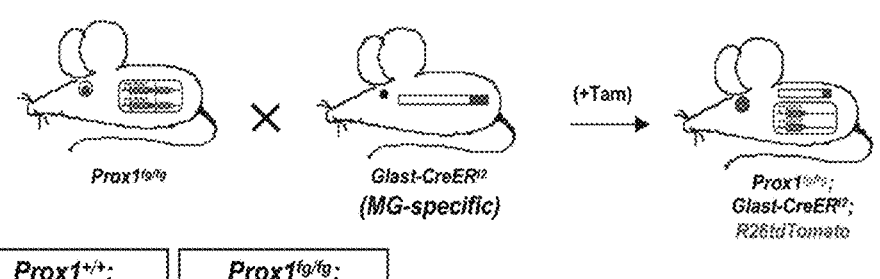
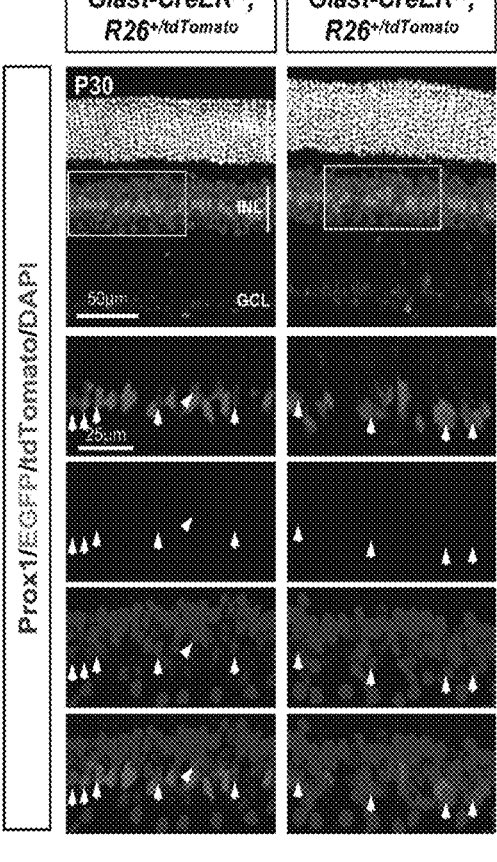
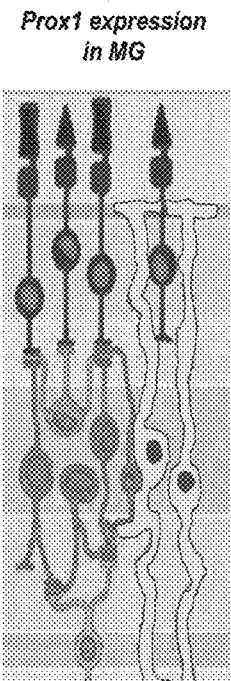
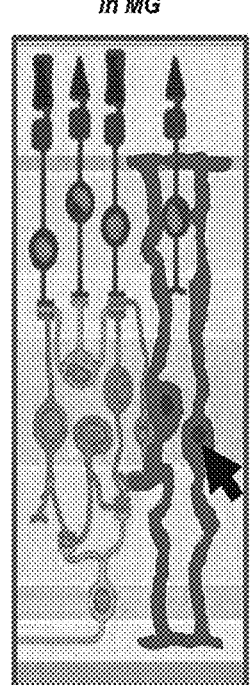

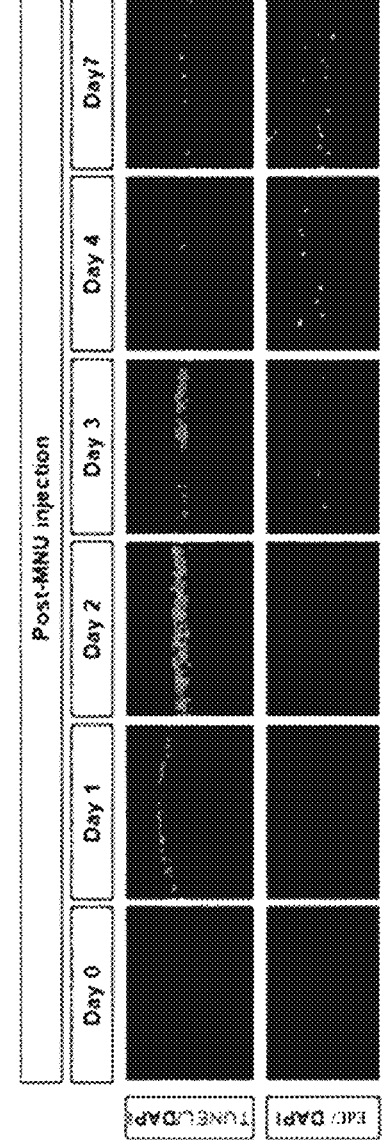
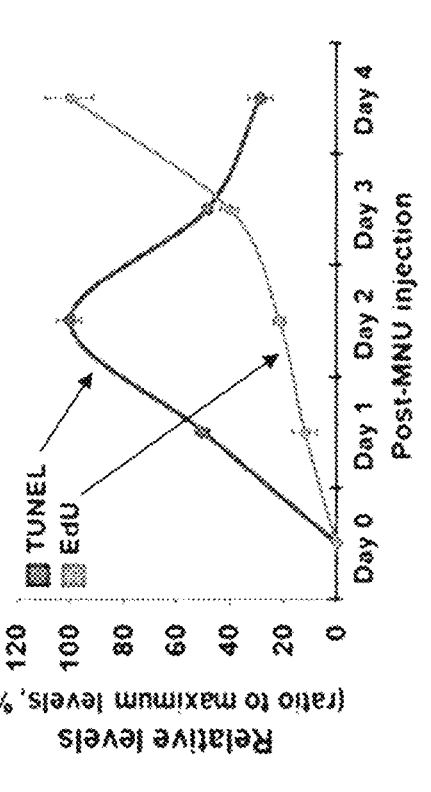
[Fig. 2a]

[Fig. 2b]
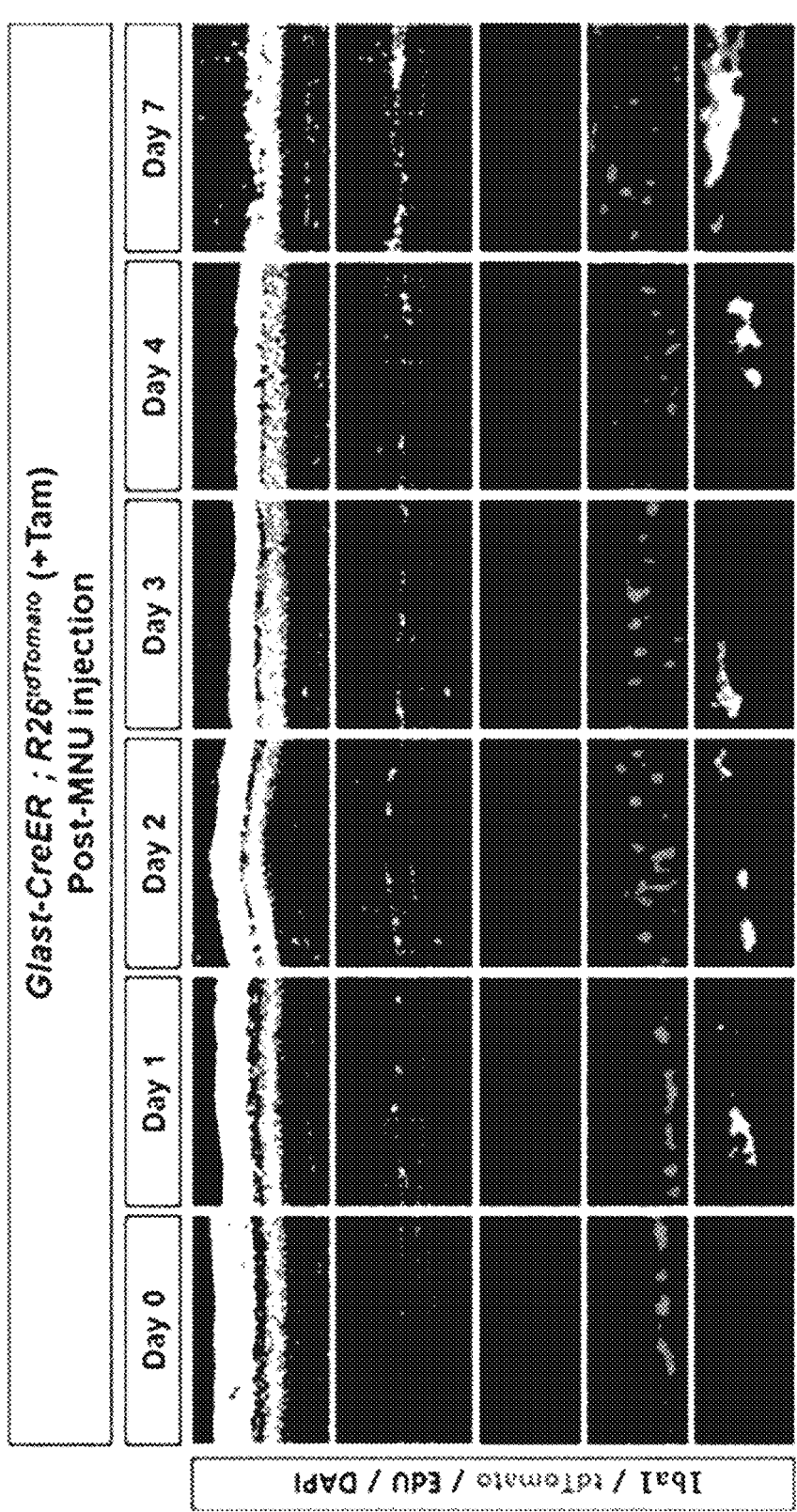

[Fig. 2c]
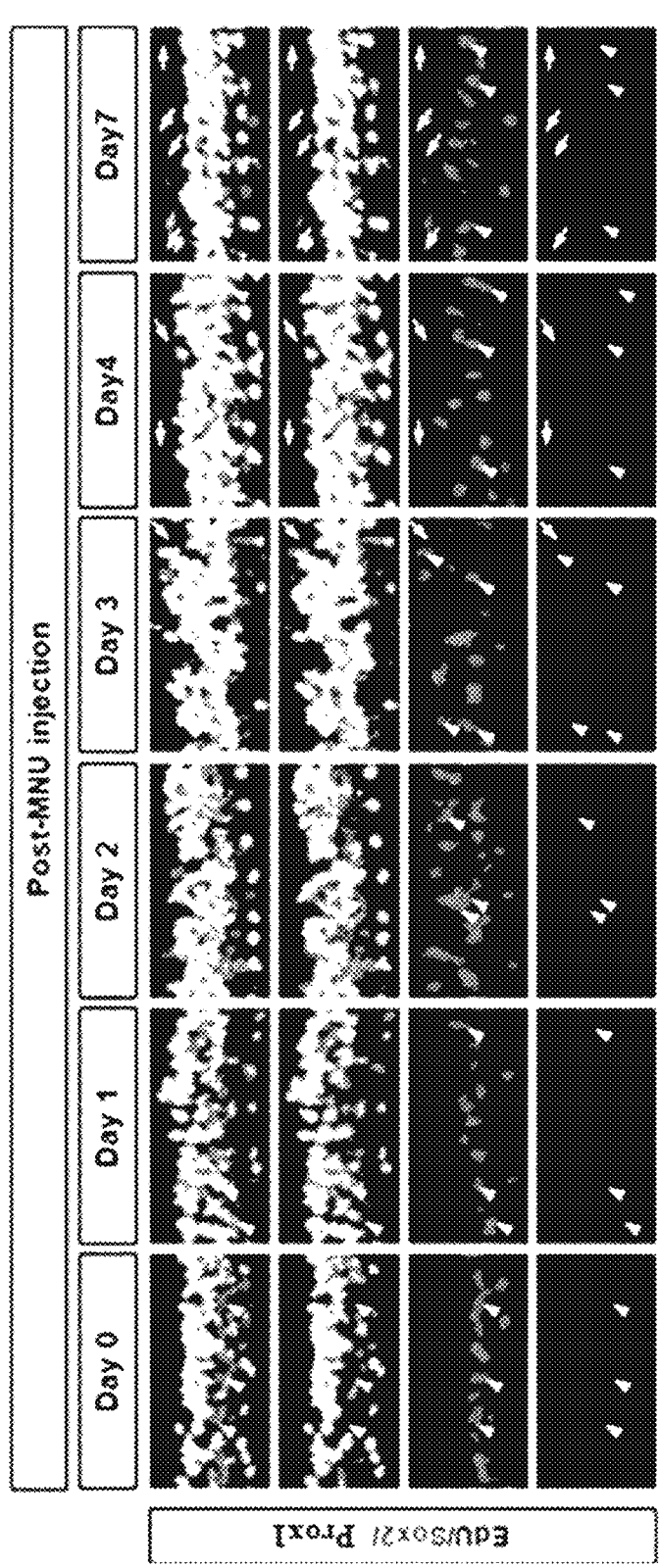

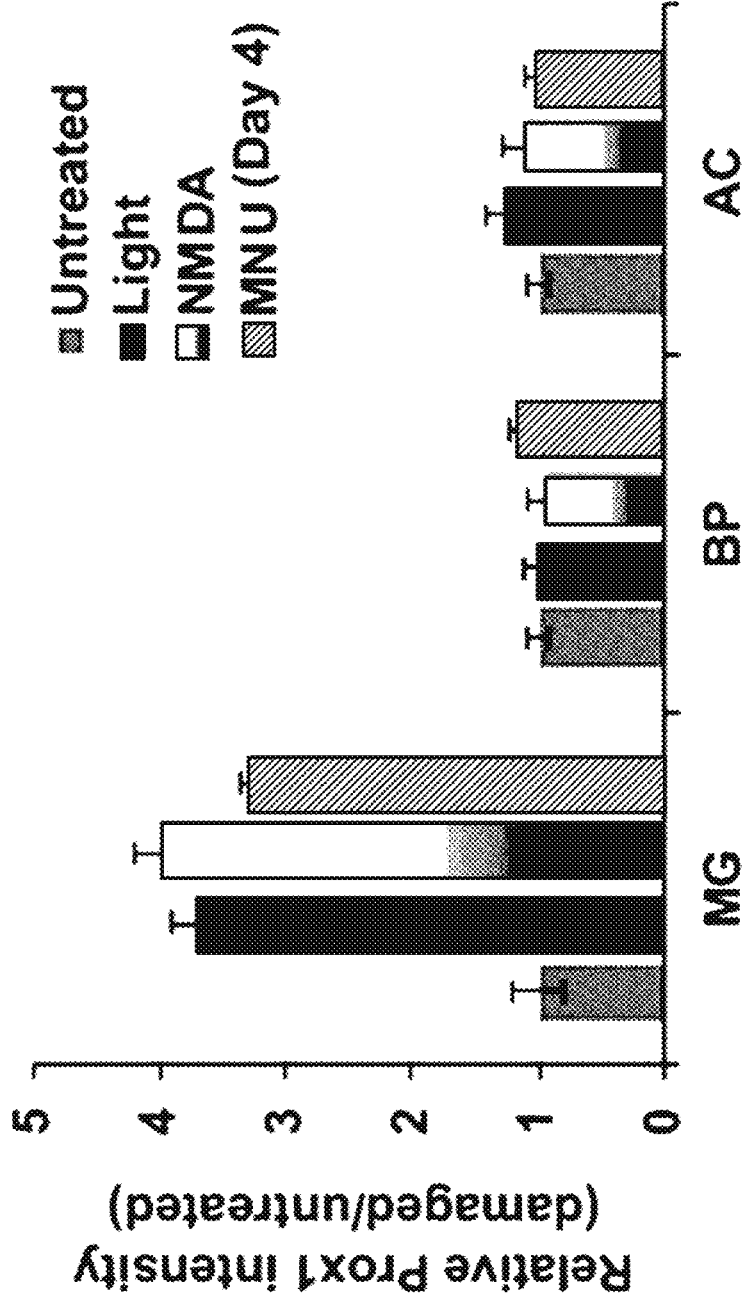
[Fig. 2d]

【Fig. 2e】
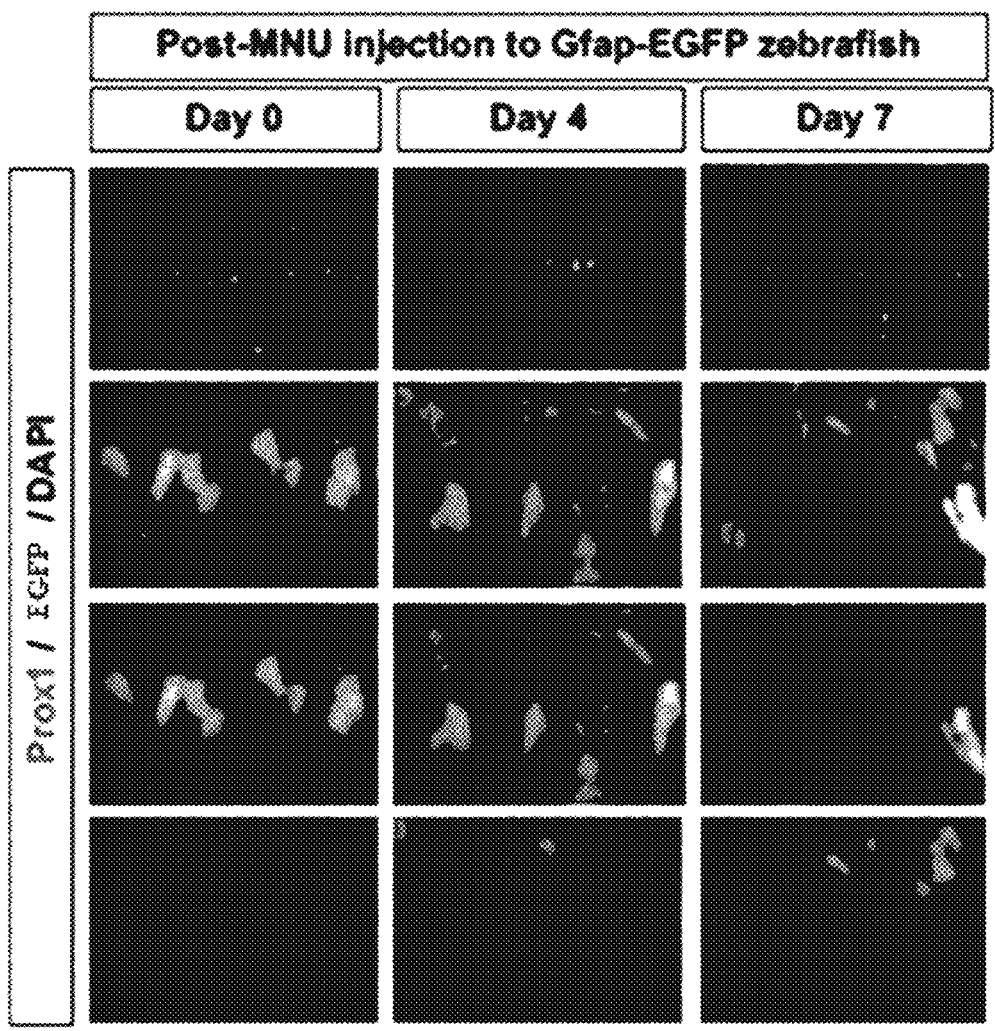

【Fig. 2f】
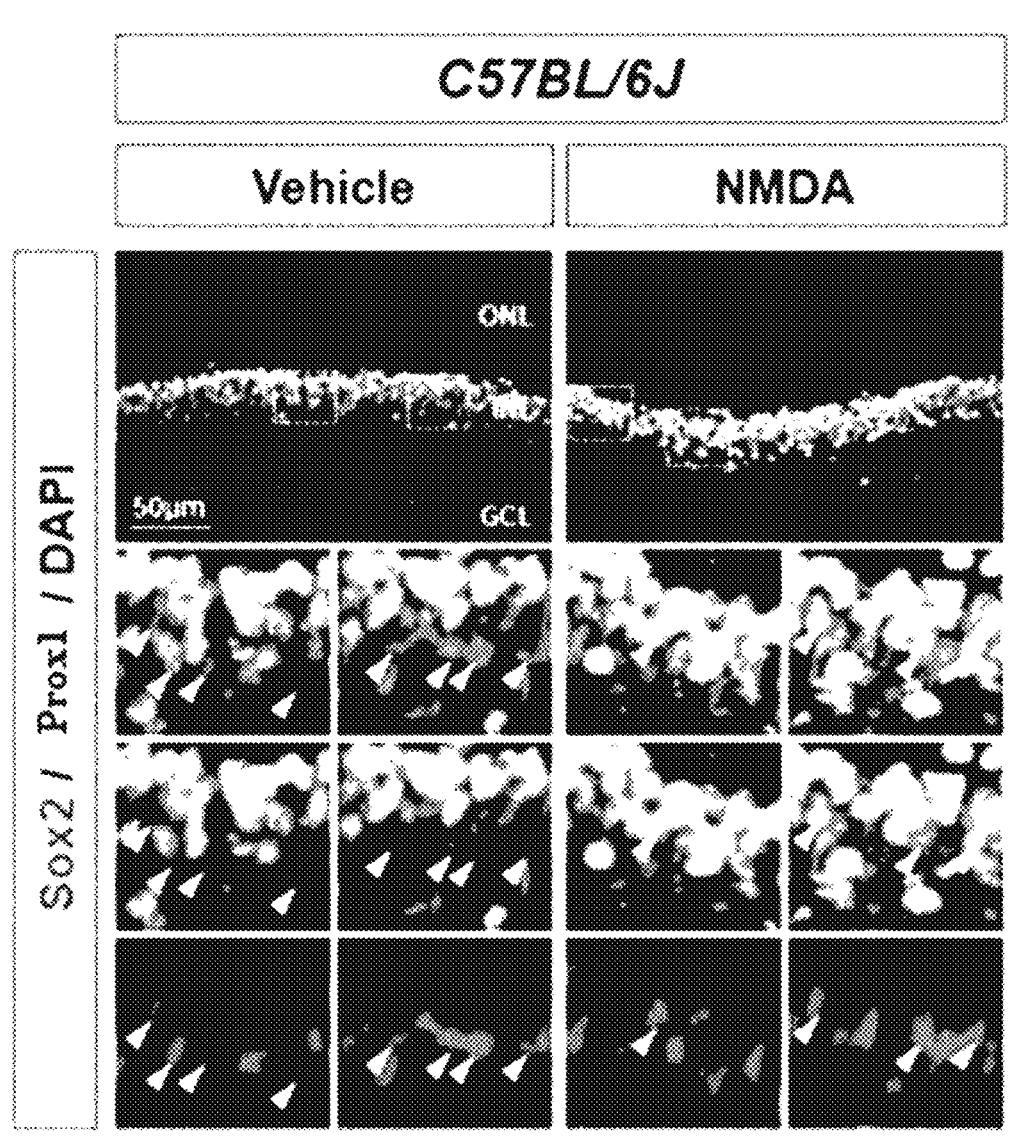

【Fig. 2g】
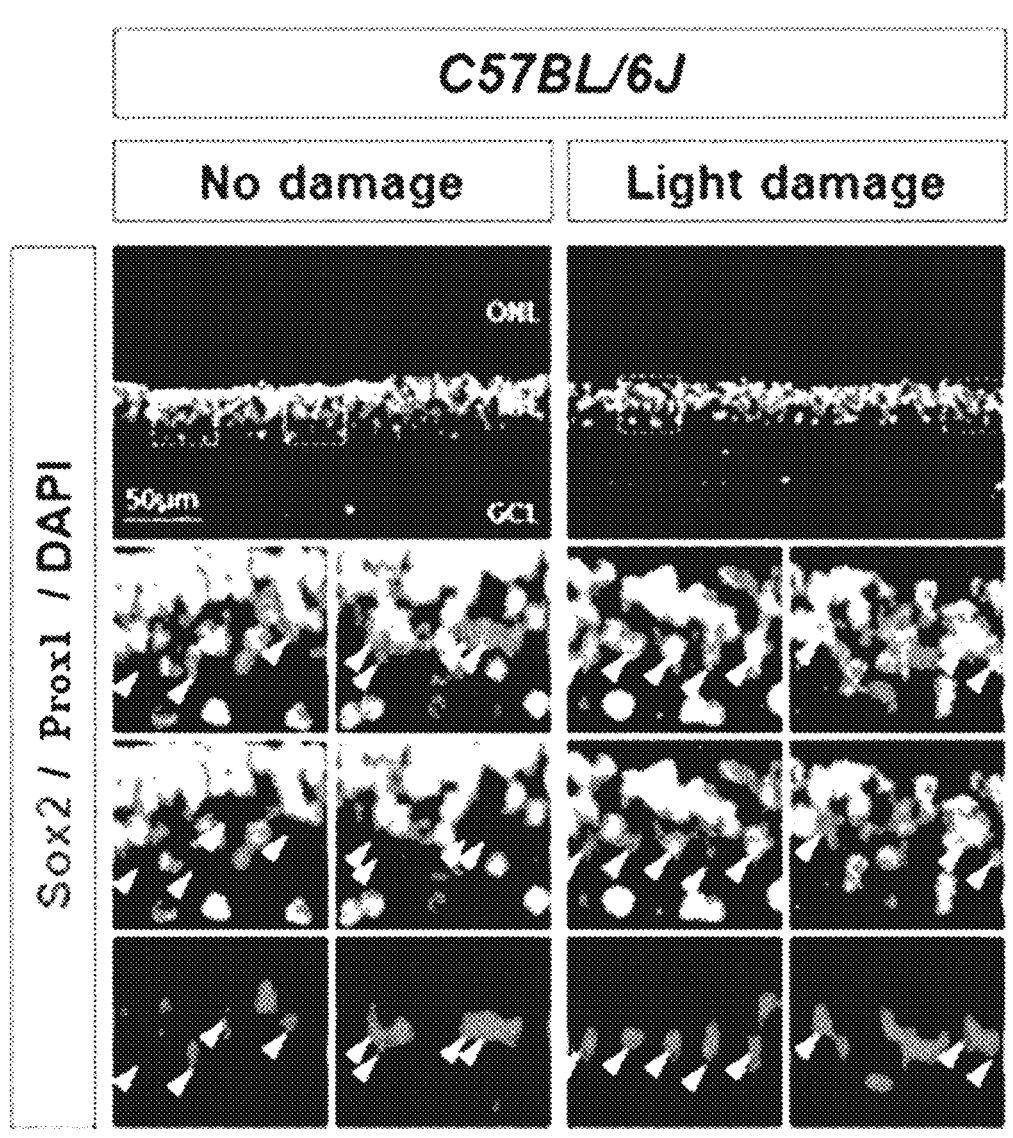

【Fig. 3a】
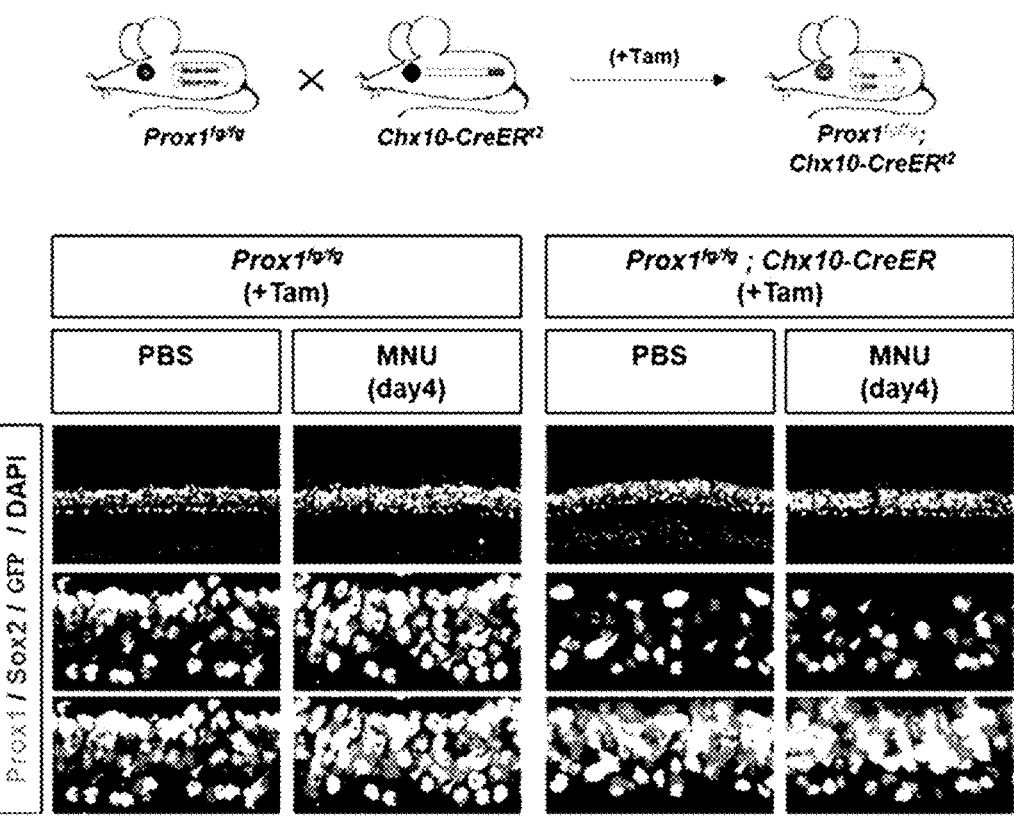

【Fig. 3b】
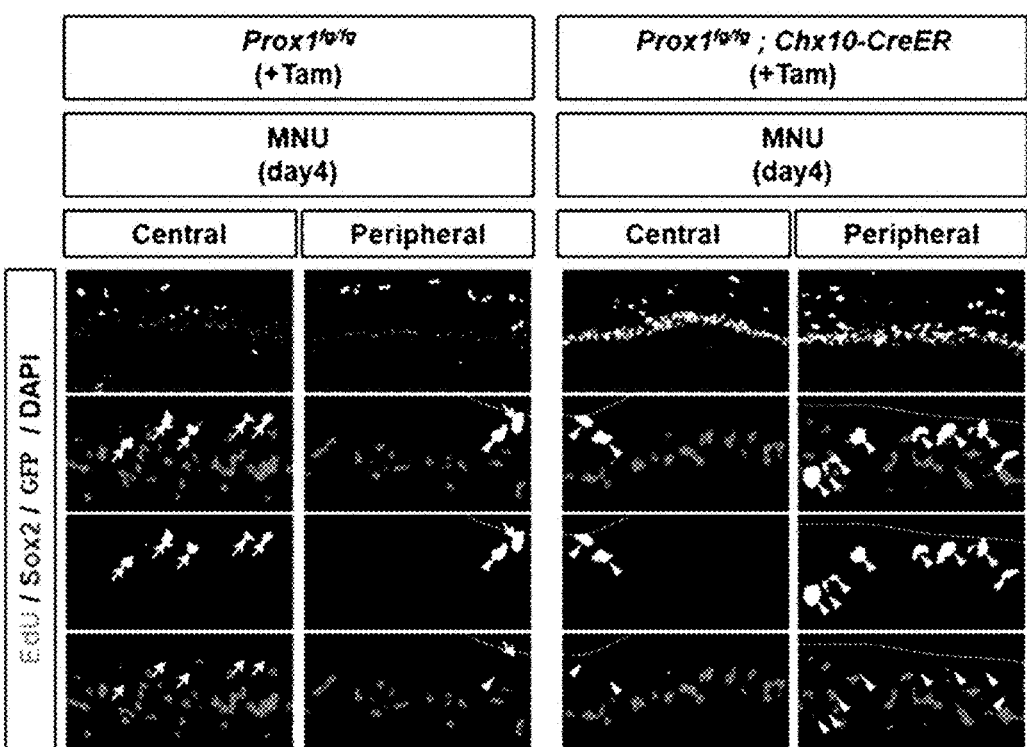

[Fig. 3c]
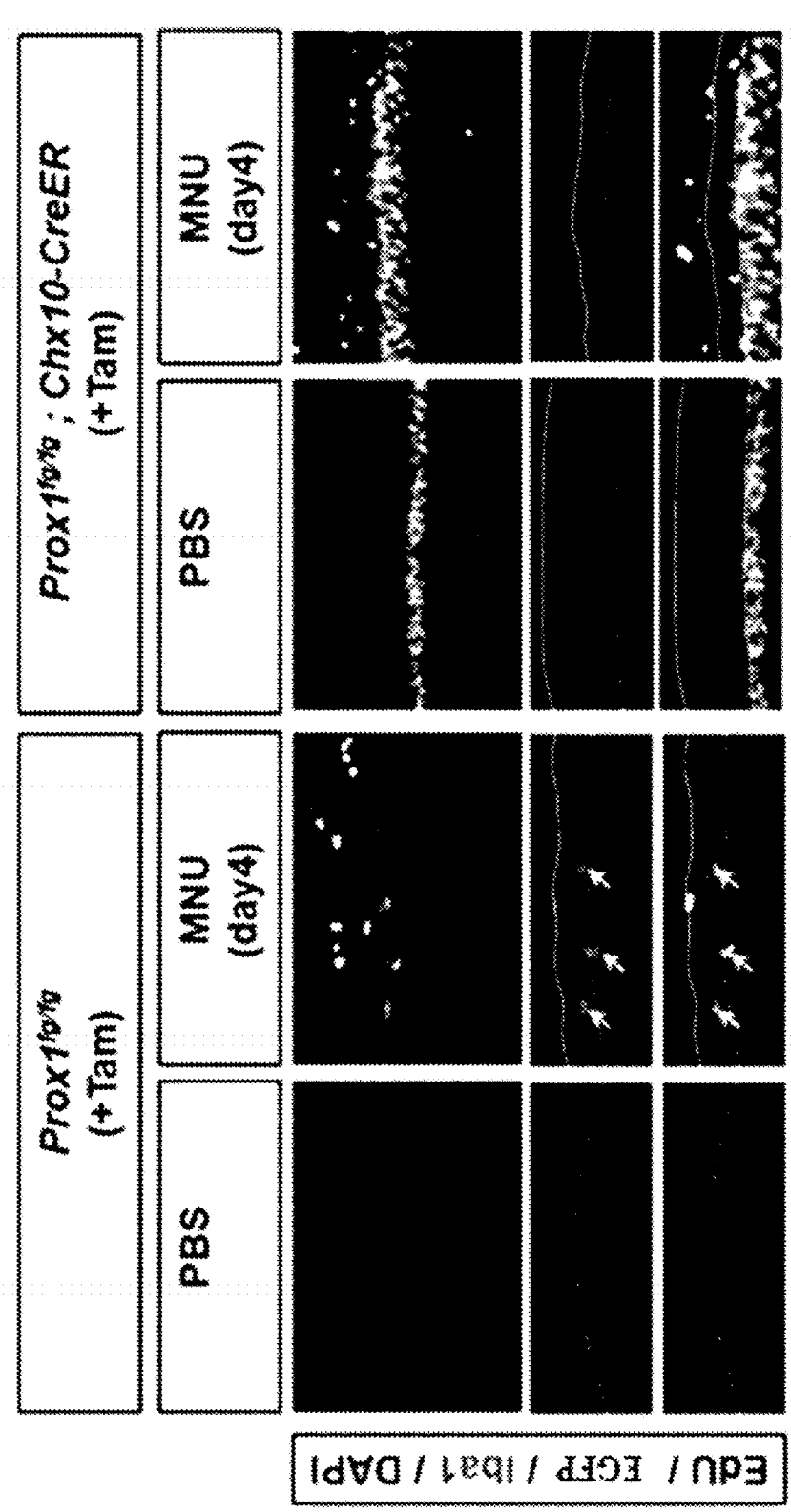

SEQUENCE LISTING

```
<160> NUMBER OF SEQ ID NOS: 4

<210> SEQ ID NO 1
<211> LENGTH: 2214
<212> TYPE: DNA
<213> ORGANISM: Homo sapiens

<400> SEQUENCE: 1
atgcctgacc atgacagcac agccctctta agccggcaaa ccaagaggag aaagagttgac      60 attggagtga aaaggacggt agggacagca tctgcatttt ttgctaaggc aagagcaacg     120
ttttttagtg ccatgaatcc ccaaggttct gagcaggatg ttgagtattc agtggtgcag     180
catgcagatg gggaaaagtc aaatgtactc cgcaagctgc tgaagagggc gaactcgtat     240
gaagatgcca tgatgccttt tccaggagca accataattt cccagctgtt gaaaaataac     300
atgaacaaaa atggtggcac ggagcccagt ttccaagcca gcggtctctc tagtacaggc     360
tccgaagtac atcaggagga tatatgcagc aactcttcaa gagacagccc cccagagtgt     420 ctttccccctt ttggcaggcc tactatgagc cagtttgata tggatcgctt atgtgatgag     480
cacctgagag caaagcgcgc ccgggttgag aatataattc ggggtatgag ccattccccc     540
agtgtggcat taaggggcaa tgaaaatgaa agagagatgg ccccgcagtc tgtgagtccc     600
cgagaaagtt acagagaaaa caaacgcaag caaaagcttc cccagcagca gcaacagagt     660
ttccagcagc tggtttcagc ccgaaaagaa cagaagcgag aggagcgccg acagctgaaa     720
```

-continued

```
cagcagctgg aggacatgca gaaacagctg cgccagctgc aggaaaagtt ctaccaaatc      780
tatgacagca ctgattcgga aaatgatgaa gatggtaacc tgtctgaaga cagcatgcgc      840
tcggagatcc tggatgccag ggcccaggac tctgtcggaa ggtcagataa tgagatgtgc      900
gagctagacc caggacagtt tattgaccga gctcgagccc tgatcagaga gcaggaaatg      960
gctgaaaaca agccgaagcg agaaggcaac aacaaagaaa gagaccatgg gccaaactcc     1020
ttacaaccgg aaggcaaaca tttggctgag accttgaaac aggaactgaa cactgccatg     1080
tcgcaagttg tggacactgt ggtcaaagtc ttttcggcca gccctcccg ccaggttcct     1140 caggtcttcc cacctctcca gatcccccag gccagatttg cagtcaatgg ggaaaaccac     1200
aatttccaca ccgccaacca gcgcctgcag tgctttggcg acgtcatcat tccgaacccc     1260
ctggacacct ttggcaatgt gcagatggcc agttccactg accagacaga agcactgccc     1320
ctggttgtcc gcaaaaactc ctctgaccag tctgcctccg gccctgccgc tggcggccac     1380
caccagcccc tgcaccagtc gcctctctct gccaccacgg gcttcaccac gtccaccttc     1440
cgccacccct tccccttcc cttgatggcc tatccatttc agagcccatt aggtgctccc     1500
tccggctcct tctctggaaa agacagagcc tctcctgaat ccttagactt aactagggat     1560
accacgagtc tgaggaccaa gatgtcatct caccacctga gccaccaccc ttgttcacca     1620
gcacacccgc ccagcaccgc cgaagggctc tccttgtcgc tcataaagtc cgagtgcggc     1680
gatcttcaag atatgtctga aatatcacct tattcgggaa gtgcaatgca ggaaggattg     1740
tcacccaatc acttgaaaaa agcaaagctc atgttttttt atacccgtta tcccagctcc     1800
aatatgctga agacctactt ctccgacgta aagttcaaca gatgcattac ctctcagctc     1860
atcaagtggt ttagcaattt ccgtgagttt tactacattc agatggagaa gtacgcacgt     1920
caagccatca cgatggggt caccagtact gaagagctgt ctataaccag agactgtgag     1980
ctgtacaggg ctctgaacat gcactacaat aaagcaaatg actttgaggt tccagagaga     2040
ttcctggaag ttgctcagat cacattacgg gagtttttca atgccattat cgcaggcaaa     2100
gatgttgatc cttcctggaa gaaggccata tacaaggtca tctgcaagct ggatagtgaa     2160
gtccctgaga ttttcaaatc cccgaactgc ctacaagagc tgcttcatga gtag           2214
```

<210> SEQ ID NO 2
<211> LENGTH: 737
<212> TYPE: PRT
<213> ORGANISM: Homo sapiens

<400> SEQUENCE: 2

```
Met Pro Asp His Asp Ser Thr Ala Leu Leu Ser Arg Gln Thr Lys Arg
1               5                   10                  15

Arg Arg Val Asp Ile Gly Val Lys Arg Thr Val Gly Thr Ala Ser Ala
            20                  25                  30

Phe Phe Ala Lys Ala Arg Ala Thr Phe Phe Ser Ala Met Asn Pro Gln
        35                  40                  45

Gly Ser Glu Gln Asp Val Glu Tyr Ser Val Val Gln His Ala Asp Gly
    50                  55                  60

Glu Lys Ser Asn Val Leu Arg Lys Leu Leu Lys Arg Ala Asn Ser Tyr
65                  70                  75                  80

Glu Asp Ala Met Met Pro Phe Pro Gly Ala Thr Ile Ile Ser Gln Leu
                85                  90                  95

Leu Lys Asn Asn Met Asn Lys Asn Gly Gly Thr Glu Pro Ser Phe Gln
            100                 105                 110
```

-continued

```
Ala Ser Gly Leu Ser Ser Thr Gly Ser Glu Val His Gln Glu Asp Ile
        115                 120                 125

Cys Ser Asn Ser Ser Arg Asp Ser Pro Pro Glu Cys Leu Ser Pro Phe
        130                 135                 140

Gly Arg Pro Thr Met Ser Gln Phe Asp Met Asp Arg Leu Cys Asp Glu
145                 150                 155                 160

His Leu Arg Ala Lys Arg Ala Arg Val Glu Asn Ile Ile Arg Gly Met
                165                 170                 175

Ser His Ser Pro Ser Val Ala Leu Arg Gly Asn Glu Asn Glu Arg Glu
                180                 185                 190

Met Ala Pro Gln Ser Val Ser Pro Arg Glu Ser Tyr Arg Glu Asn Lys
        195                 200                 205

Arg Lys Gln Lys Leu Pro Gln Gln Gln Gln Ser Phe Gln Gln Leu
        210                 215                 220

Val Ser Ala Arg Lys Glu Gln Lys Arg Glu Glu Arg Arg Gln Leu Lys
225                 230                 235                 240

Gln Gln Leu Glu Asp Met Gln Lys Gln Leu Arg Gln Leu Gln Glu Lys
                245                 250                 255

Phe Tyr Gln Ile Tyr Asp Ser Thr Asp Ser Glu Asn Asp Glu Asp Gly
                260                 265                 270

Asn Leu Ser Glu Asp Ser Met Arg Ser Glu Ile Leu Asp Ala Arg Ala
        275                 280                 285

Gln Asp Ser Val Gly Arg Ser Asp Asn Glu Met Cys Glu Leu Asp Pro
        290                 295                 300

Gly Gln Phe Ile Asp Arg Ala Arg Ala Leu Ile Arg Glu Gln Glu Met
305                 310                 315                 320

Ala Glu Asn Lys Pro Lys Arg Glu Gly Asn Asn Lys Glu Arg Asp His
                325                 330                 335

Gly Pro Asn Ser Leu Gln Pro Glu Gly Lys His Leu Ala Glu Thr Leu
                340                 345                 350

Lys Gln Glu Leu Asn Thr Ala Met Ser Gln Val Val Asp Thr Val Val
                355                 360                 365

Lys Val Phe Ser Ala Lys Pro Ser Arg Gln Val Pro Gln Val Phe Pro
        370                 375                 380

Pro Leu Gln Ile Pro Gln Ala Arg Phe Ala Val Asn Gly Glu Asn His
385                 390                 395                 400

Asn Phe His Thr Ala Asn Gln Arg Leu Gln Cys Phe Gly Asp Val Ile
                405                 410                 415

Ile Pro Asn Pro Leu Asp Thr Phe Gly Asn Val Gln Met Ala Ser Ser
                420                 425                 430

Thr Asp Gln Thr Glu Ala Leu Pro Leu Val Val Arg Lys Asn Ser Ser
        435                 440                 445

Asp Gln Ser Ala Ser Gly Pro Ala Ala Gly Gly His His Gln Pro Leu
        450                 455                 460

His Gln Ser Pro Leu Ser Ala Thr Thr Gly Phe Thr Thr Ser Thr Phe
465                 470                 475                 480

Arg His Pro Phe Pro Leu Pro Leu Met Ala Tyr Pro Phe Gln Ser Pro
                485                 490                 495

Leu Gly Ala Pro Ser Gly Ser Phe Ser Gly Lys Asp Arg Ala Ser Pro
                500                 505                 510

Glu Ser Leu Asp Leu Thr Arg Asp Thr Thr Ser Leu Arg Thr Lys Met
        515                 520                 525
```

-continued

```
Ser Ser His His Leu Ser His His Pro Cys Ser Pro Ala His Pro Pro
    530                 535                 540
```

```
Ser Thr Ala Glu Gly Leu Ser Leu Ser Leu Ile Lys Ser Glu Cys Gly
545                 550                 555                 560
```

```
Asp Leu Gln Asp Met Ser Glu Ile Ser Pro Tyr Ser Gly Ser Ala Met
                565                 570                 575
```

```
Gln Glu Gly Leu Ser Pro Asn His Leu Lys Lys Ala Lys Leu Met Phe
            580                 585                 590
```

```
Phe Tyr Thr Arg Tyr Pro Ser Ser Asn Met Leu Lys Thr Tyr Phe Ser
        595                 600                 605
```

```
Asp Val Lys Phe Asn Arg Cys Ile Thr Ser Gln Leu Ile Lys Trp Phe
    610                 615                 620
```

```
Ser Asn Phe Arg Glu Phe Tyr Tyr Ile Gln Met Glu Lys Tyr Ala Arg
625                 630                 635                 640
```

```
Gln Ala Ile Asn Asp Gly Val Thr Ser Thr Glu Glu Leu Ser Ile Thr
                645                 650                 655
```

```
Arg Asp Cys Glu Leu Tyr Arg Ala Leu Asn Met His Tyr Asn Lys Ala
            660                 665                 670
```

```
Asn Asp Phe Glu Val Pro Glu Arg Phe Leu Glu Val Ala Gln Ile Thr
        675                 680                 685
```

```
Leu Arg Glu Phe Phe Asn Ala Ile Ile Ala Gly Lys Asp Val Asp Pro
    690                 695                 700
```

```
Ser Trp Lys Lys Ala Ile Tyr Lys Val Ile Cys Lys Leu Asp Ser Glu
705                 710                 715                 720
```

```
Val Pro Glu Ile Phe Lys Ser Pro Asn Cys Leu Gln Glu Leu Leu His
                725                 730                 735
```

```
Glu
```

<210> SEQ ID NO 3
<211> LENGTH: 2214
<212> TYPE: DNA
<213> ORGANISM: Mus musculus

<400> SEQUENCE: 3

```
atgcctgacc atgacagcac agccctctta agccggcaaa ccaagaggag aagggttgac      60
attggagtga aaaggacggt agggacagca tctgcatttt ttgctaaggc aagggcaaca     120
tttttcagtg ccatgaatcc ccaaggttca gagcaggatg ttgaatattc tgtggtgcaa     180
cacgcagatg gggaaaagtc gaacgtactc cgcaagctgc tgaagagggc gaactcgtat     240
gaagatgcca tgatgccttt ccaggagca actataattt cccagctgtt gaaaaataac     300
atgaacaaaa acggtggcac cgagcccagt ttccaagcca gcggactctc tagcacaggc     360
tccgaagtac atcaggagga tatatgtagc aactcttcaa gagacagccc cccagagtgt     420
ctttcccctt ttggcaggcc tactatgagc cagtttgatg tggatcgctt atgtgatgag     480
cacctgagag caaagcgggc ccgggttgag aatatcattc ggggtatgag ccattccccc     540
agtgtggcat taaggggcaa tgaaaatgaa agagagatgg ccccgcagtc tgtgagtccc     600
cgagaaagtt acagagaaaa caaacgcaag cagaagctgc cccagcagca gcaacagagt     660
ttccagcagc tggtttcagc ccgaaaagaa cagaagcgag aggagcgccg acagctgaaa     720
cagcagctgg aagacatgca gaagcagctg cgccagctgc aggagaagtt ctaccaggtc     780
tatgacagca cagactccga aaatgatgaa gatggcgacc tgtctgaaga cagcatgcgc     840
tcggagatcc tggatgcacg ggcccaggac tcggtggggc gctcagacaa tgagatgtgt     900
```

-continued

```
gagctggacc cagggcagtt catcgacagg gcccgagccc taatcaggga gcaggagatg      960
gctgagaaca agcctaagcg agaaggcagc aacaaagaaa gagaccacgg gccaaactcc     1020
ttgcagccag aaggcaagca tctggcagag accttaaaac aggagctgaa cacggccatg     1080
tcgcaggtcg tggacacggt ggtcaaagtc ttctcagcca aaccctctcg ccaggttcct     1140
caggtcttcc cacctctcca gatcccccag gccagattcg cagtcaacgg ggaaaaccac     1200
aatttccaca cggccaacca gcgcctgcaa tgctttggtg atgtcatcat tccgaacccc     1260
ttggacacct ttggcagtgt gcagatgcct agttccacag accagacgga agcccttccc     1320
ctggtggtcc gaaaaaactc atccgagcaa tctgcctctg gcccggccac tggcggccac     1380
caccagcccc tgcaccagtc acccctctcc gccactgcag gcttcaccac ccctagcttc     1440
cgccatccct ttcccctgcc cttgatggct tatccatttc agagtccact aggtgctccc     1500
tccggctcct tctcggggaa ggacagagcc tctcctgagt ccttagactt gactcgggac     1560
acaacaagtc tgaggaccaa gatgtcatca caccatctga gccaccaccc ctgttcacca     1620
gcacacccac ccagcaccgc agaaggactc tctttgtcac tcataaagtc tgagtgtgga     1680
gatcttcaag atatgtccga catctccacct tattcaggaa gcgcaatgca ggaagggcta     1740
tcacccaatc acttgaaaaa ggcaaaactc atgttctttt acacccgcta ccccagctcc     1800
aacatgctga agacctactt ctcggacgtg aagttcaaca gatgcattac ctcgcagctc     1860
atcaagtggt tcagcaattt ccgtgagttt tactatatcc agatggagaa gtatgcgcgt     1920
caagccatca atgatggagt caccagtaca gaagagctct ccatcaccag ggattgtgaa     1980
ctataccgag ccctcaacat gcactacaac aaagcaaatg actttgaggt tccagagaga     2040
ttcctggaag ttgcgcagat cacgttacgg gagtttttca atgccatcat cgcgggcaaa     2100
gatgttgatc cttcctggaa gaaggccatt tacaaggtca tctgcaagct ggatagtgaa     2160
gttcctgaga ttttcaaatc ccctaactgc ctacaagaac tccttcacga gtag          2214
```

<210> SEQ ID NO 4
<211> LENGTH: 737
<212> TYPE: PRT
<213> ORGANISM: Mus musculus

<400> SEQUENCE: 4

```
Met Pro Asp His Asp Ser Thr Ala Leu Leu Ser Arg Gln Thr Lys Arg
1               5                   10                  15

Arg Arg Val Asp Ile Gly Val Lys Arg Thr Val Gly Thr Ala Ser Ala
            20                  25                  30

Phe Phe Ala Lys Ala Arg Ala Thr Phe Phe Ser Ala Met Asn Pro Gln
        35                  40                  45

Gly Ser Glu Gln Asp Val Glu Tyr Ser Val Val Gln His Ala Asp Gly
    50                  55                  60

Glu Lys Ser Asn Val Leu Arg Lys Leu Leu Lys Arg Ala Asn Ser Tyr
65                  70                  75                  80

Glu Asp Ala Met Met Pro Phe Pro Gly Ala Thr Ile Ile Ser Gln Leu
                85                  90                  95

Leu Lys Asn Asn Met Asn Lys Asn Gly Gly Thr Glu Pro Ser Phe Gln
            100                 105                 110

Ala Ser Gly Leu Ser Ser Thr Gly Ser Glu Val His Gln Glu Asp Ile
        115                 120                 125

Cys Ser Asn Ser Ser Arg Asp Ser Pro Pro Glu Cys Leu Ser Pro Phe
    130                 135                 140
```

```
Gly Arg Pro Thr Met Ser Gln Phe Asp Val Asp Arg Leu Cys Asp Glu
145                 150                 155                 160

His Leu Arg Ala Lys Arg Ala Arg Val Glu Asn Ile Ile Arg Gly Met
                165                 170                 175

Ser His Ser Pro Ser Val Ala Leu Arg Gly Asn Glu Asn Glu Arg Glu
                180                 185                 190

Met Ala Pro Gln Ser Val Ser Pro Arg Glu Ser Tyr Arg Glu Asn Lys
                195                 200                 205

Arg Lys Gln Lys Leu Pro Gln Gln Gln Gln Ser Phe Gln Gln Leu
                210                 215                 220

Val Ser Ala Arg Lys Glu Gln Lys Arg Glu Glu Arg Arg Gln Leu Lys
225                 230                 235                 240

Gln Gln Leu Glu Asp Met Gln Lys Gln Leu Arg Gln Leu Gln Glu Lys
                245                 250                 255

Phe Tyr Gln Val Tyr Asp Ser Thr Asp Ser Glu Asn Asp Glu Asp Gly
                260                 265                 270

Asp Leu Ser Glu Asp Ser Met Arg Ser Glu Ile Leu Asp Ala Arg Ala
                275                 280                 285

Gln Asp Ser Val Gly Arg Ser Asp Asn Glu Met Cys Glu Leu Asp Pro
                290                 295                 300

Gly Gln Phe Ile Asp Arg Ala Arg Ala Leu Ile Arg Glu Gln Glu Met
305                 310                 315                 320

Ala Glu Asn Lys Pro Lys Arg Glu Gly Ser Asn Lys Glu Arg Asp His
                325                 330                 335

Gly Pro Asn Ser Leu Gln Pro Glu Gly Lys His Leu Ala Glu Thr Leu
                340                 345                 350

Lys Gln Glu Leu Asn Thr Ala Met Ser Gln Val Val Asp Thr Val Val
                355                 360                 365

Lys Val Phe Ser Ala Lys Pro Ser Arg Gln Val Pro Gln Val Phe Pro
                370                 375                 380

Pro Leu Gln Ile Pro Gln Ala Arg Phe Ala Val Asn Gly Glu Asn His
385                 390                 395                 400

Asn Phe His Thr Ala Asn Gln Arg Leu Gln Cys Phe Gly Asp Val Ile
                405                 410                 415

Ile Pro Asn Pro Leu Asp Thr Phe Gly Ser Val Gln Met Pro Ser Ser
                420                 425                 430

Thr Asp Gln Thr Glu Ala Leu Pro Leu Val Val Arg Lys Asn Ser Ser
                435                 440                 445

Glu Gln Ser Ala Ser Gly Pro Ala Thr Gly Gly His His Gln Pro Leu
                450                 455                 460

His Gln Ser Pro Leu Ser Ala Thr Ala Gly Phe Thr Thr Pro Ser Phe
465                 470                 475                 480

Arg His Pro Phe Pro Leu Pro Leu Met Ala Tyr Pro Phe Gln Ser Pro
                485                 490                 495

Leu Gly Ala Pro Ser Gly Ser Phe Ser Gly Lys Asp Arg Ala Ser Pro
                500                 505                 510

Glu Ser Leu Asp Leu Thr Arg Asp Thr Thr Ser Leu Arg Thr Lys Met
                515                 520                 525

Ser Ser His His Leu Ser His His Pro Cys Ser Pro Ala His Pro Pro
                530                 535                 540

Ser Thr Ala Glu Gly Leu Ser Leu Ser Leu Ile Lys Ser Glu Cys Gly
545                 550                 555                 560
```

-continued

```
Asp Leu Gln Asp Met Ser Asp Ile Ser Pro Tyr Ser Gly Ser Ala Met
                565             570             575

Gln Glu Gly Leu Ser Pro Asn His Leu Lys Lys Ala Lys Leu Met Phe
            580             585             590

Phe Tyr Thr Arg Tyr Pro Ser Ser Asn Met Leu Lys Thr Tyr Phe Ser
        595             600             605

Asp Val Lys Phe Asn Arg Cys Ile Thr Ser Gln Leu Ile Lys Trp Phe
    610             615             620

Ser Asn Phe Arg Glu Phe Tyr Tyr Ile Gln Met Glu Lys Tyr Ala Arg
625             630             635             640

Gln Ala Ile Asn Asp Gly Val Thr Ser Thr Glu Glu Leu Ser Ile Thr
            645             650             655

Arg Asp Cys Glu Leu Tyr Arg Ala Leu Asn Met His Tyr Asn Lys Ala
            660             665             670

Asn Asp Phe Glu Val Pro Glu Arg Phe Leu Glu Val Ala Gln Ile Thr
        675             680             685

Leu Arg Glu Phe Phe Asn Ala Ile Ile Ala Gly Lys Asp Val Asp Pro
    690             695             700

Ser Trp Lys Lys Ala Ile Tyr Lys Val Ile Cys Lys Leu Asp Ser Glu
705             710             715             720

Val Pro Glu Ile Phe Lys Ser Pro Asn Cys Leu Gln Glu Leu Leu His
            725             730             735

Glu
```

METHODS AND COMPOSITIONS TO PROMOTING RETINAL REGENERATION USING PROX1 MIGRATION INHIBITOR AS ACTIVE INGREDIENT

RELATED APPLICATIONS

The present invention is a Continuation of PCT Serial No. PCT/KR2021/008044, filed on Jun. 25, 2021, which claims priority from Korean Patent Application No. 10-2020-0078016 filed on Jun. 25, 2020 and Korean Patent Application No. 10-2021-0077060 filed on Jun. 14, 2021; the entireties of both are hereby incorporated herein by reference.

TECHNICAL FIELD

The present invention relates to a technique capable of treating a retinal neurodegenerative disease through regeneration of the retinal nerve in the mammalian retina, and more specifically, to a pharmaceutical composition for preventing or treating a retinal neurodegenerative disease, comprising a Prox1 expression or migration inhibitor as an active ingredient and a pharmaceutical preparation comprising the composition.

BACKGROUND ART

The retina is a transparent nerve tissue that covers the innermost part of the eyeball, and the light entering the eyeball passes through the inner layer of the retina and is detected by the visual cells of the retina. The visual cells convert light information back into electrical information, which passes through neurons and optic nerves of the inner layer of the retina, allowing us to see things through this process. The outermost part of the eyeball is an avascular fibrous layer (cornea, sclera), and the intermediate layer is a vascular tissue, the uvea (iris, ciliary body, choroid), and the clear nerve tissue that covers the inside of the intermediate layer, the choroid, is the retina. The retina is a thin, transparent membrane with a varying thickness, and the central part of the retina is subdivided into the fovea, parafovea, and perifovea, depending on the position. The fovea is clinically called the macula.

Meanwhile, a retinal neurodegenerative disease may occur due to congenital or acquired damage to the retina or complications of a chronic disease such as hypertension and diabetes. Specific examples thereof include a congenital retinal degenerative disease such as retinitis pigmentosa, which shows nyctalopia which is an inability to see well in the dark as an initial symptom and Leber congenital amaurosis (LCA) which is hereditary retinal dystrophy, retinal detachment in which the retina tears and peels away, macular degeneration, diabetic retinopathy caused by diabetes, central serous retinopathy, senile retinal degeneration, and the like. Due to these diseases, symptoms such as decreased vision acuity, nyctalopia including visual field disturbances, color amblyopia, color blindness, photopsia (lights appear to flash when moving eyes), myodesopsia (something appears to float in front of the eyes like mayflies), metamorphopsia (an object looks bent), and central scotoma (center of visual field looks black) appear. However, unlike lower vertebrates, which are capable of regenerating retinal neurons, mammals do not regenerate retinal neurons and retinal neurons cannot be transplanted, so once damaged, the retina does not recover, and thus may result in blindness.

Despite a rapid increase in the incidence rate of such retinal neurodegenerative diseases, there are currently few effective therapeutic agents or therapeutic methods. Recently, studies on cell therapeutic agents using various stem cells for the replacement and protection of retinal cells have been conducted, but the clinical application thereof has not yet been made (Korean Patent No. 10-1268741), and Stargardt's disease gene therapy targeting retinal pigment epithelial cells has been clinically applied, but is limited only to patients with some genetic mutations, and there is no technology capable of restoring visual function by regenerating the degenerated retina.

Therefore, there is an urgent need for developing a safe and economical therapeutic agent that can be widely applied to various diseases caused by retinal degeneration in mammals including humans who are fundamentally unable to regenerate retinal nerves.

DISCLOSURE

Technical Problem

As a result of intensive studies to develop a technology capable of inducing regeneration of a retinal nerve under the aforementioned background, the present inventors discovered a mechanism by which a Prox1 protein expressed in retinal neurons in a mammal migrates to the Muller glia after retinal damage for the first time, and based on this, confirmed that the cell division of Muller glia, which is the first stage of retinal nerve regeneration can be induced by suppressing the expression of Prox1 in the retina or migration of Prox1 from the retinal neurons to the Muller glia, thereby completing the present invention based on this.

Thus, an object of the present invention is to provide a pharmaceutical composition for preventing or treating a retinal neurodegenerative disease, comprising a prospero homeobox 1 (Prox1) inhibitor as an active ingredient.

Further, another object of the present invention is to provide a pharmaceutical preparation for preventing or treating a retinal neurodegenerative disease, comprising the composition.

However, technical problems to be solved by the present invention are not limited to the aforementioned problems, and other problems that are not mentioned may be clearly understood by the person skilled in the art from the following description.

Technical Solution

To achieve the aforementioned objects, the present invention provides a pharmaceutical composition for preventing or treating a retinal neurodegenerative disease, comprising a prospero homeobox 1 (Prox1) inhibitor as an active ingredient.

As an exemplary embodiment of the present invention, the inhibitor may suppress the expression of a Prox1 gene in retinal neurons.

As another exemplary embodiment of the present invention, the inhibitor may suppress the migration of a Prox1 protein from retinal neurons to the Muller glia.

As still another exemplary embodiment of the present invention, the Prox1 gene may include a base sequence of SEQ ID NO: 1.

As yet another exemplary embodiment of the present invention, the Prox1 protein may include an amino acid sequence of SEQ ID NO: 2.

As yet another exemplary embodiment of the present invention, the inhibitor which suppresses the expression of the Prox1 gene may be any one selected from the group consisting of an antisense nucleotide, small interfering RNA (siRNA), short hairpin RNA (shRNA), a ribozyme and CRISPR/Cas9, which complementarily bind to mRNA of the Prox1 gene.

As yet another exemplary embodiment of the present invention, the inhibitor which suppresses the migration of the Prox1 protein may be any one selected from the group consisting of antibodies, peptides, peptide analogues, aptamers and compounds, which specifically bind to the Prox1 protein or competitively suppress the binding of Prox1 and the Muller glia cell membrane.

As yet another exemplary embodiment of the present invention, the retinal neurodegenerative disease may be any one selected from the group consisting of retinitis pigmentosa, Leber congenital amaurosis (LCA), retinal detachment, macular degeneration, diabetic retinopathy, glaucoma, central serous retinopathy and senile retinal degeneration.

As yet another exemplary embodiment of the present invention, the composition may promote the regeneration of retinal neurons by suppressing the proliferation of microglia which induce phagocytosis and inflammatory responses.

As yet another exemplary embodiment of the present invention, the composition may be administered in combination with a preparation which promotes the differentiation of neurons.

Further, the present invention provides a pharmaceutical preparation for preventing or treating a retinal neurodegenerative disease, comprising the composition.

As an exemplary embodiment of the present invention, the pharmaceutical preparation may be an injection formulation, an infusion formulation, a spray formulation or a liquid formulation.

As another exemplary embodiment of the present invention, the pharmaceutical preparation may be for topical ocular administration.

In addition, the present invention provides a method for preventing or treating a retinal neurodegenerative disease, the method comprising: administering, to an individual, a pharmaceutical composition comprising a prospero homeobox 1 (Prox1) inhibitor as an active ingredient.

Furthermore, the present invention provides a use of the pharmaceutical composition for preventing or treating a retinal neurodegenerative disease.

Advantageous Effects

The present inventors discovered the migration of a Prox1 protein to the Muller glia during retinal damage for the first time, and based on this, confirmed that the division of Muller glia is possible by suppressing the expression or migration of Prox1. The division of Muller glia is a precursor of retinal regeneration, because the division of Muller glia is suppressed in the mammalian retina, in this aspect, the pharmaceutical composition comprising an inhibitor of Prox1 according to the present invention can induce the regeneration of a damaged retina in mammals, and thus can be commonly applied to the treatment of various retinal neurodegenerative diseases causing blindness because there is no effective therapeutic method in the related art, and furthermore, when the pharmaceutical composition is combined with a selective retinal nerve differentiation method or the like, it is expected that the pharmaceutical composition can be used for the development of an innovative retinal regeneration method capable of selectively regenerating only specific degenerating retinal neurons.

DESCRIPTION OF DRAWINGS

The results shown in the left column of FIG. 1A are the results showing the expression of EGFP and Prox1 proteins in the retina of transgenic mice produced using a vector in which an EGFP gene was inserted into a Prox1 gene site, the results shown in the right column of FIG. 1A are the results of simultaneously detecting Prox1 mRNA and the Prox1 protein by in situ RNA hybridization (ISH) and immunofluorescence staining, and in theory, the Prox1 protein is produced through translation of Prox1 mRNA, suggesting that cells with only the Prox1 protein without Prox1 mRNA can have been introduced from the outside.

FIG. 2A shows the results of inducing mouse retinal damage using N-methyl-N-nitrosourea (MNU), and then confirming apoptotic cells detected by TUNEL staining and newly generated cells labeled with EdU until after Day 7.

FIG. 2B shows the distribution of microglia labeled with Iba1 in the mouse retina damaged by MNU.

FIG. 2C shows the results of comparing cells in which Muller glia and Prox1 labeled with Sox2 are present by immunofluorescence staining after performing a retinal damage experiment under the same conditions as in FIG. 2B.

FIG. 2D shows the results of comparing the amounts of Prox1 proteins in Muller glia (MG), bipolar cells (BP) and amacrine cells (AC) that make up the retina under each retinal damage condition including MNU administration.

FIG. 2E shows the results of confirming the distribution of Muller glia and Prox1 labeled with Gfap-EGFP transgene after inducing retinal damage by administering MNU to zebrafish.

FIG. 2F shows the results of comparing cells in which Muller glia and Prox1 labeled with Sox2 are present after inducing retinal damage by treatment with N-methyl-D-aspartic acid (NMDA).

FIG. 2G shows the results of confirming the distribution of Prox1 in Muller glia cells after inducing retinal damage by exposing the retina to strong light for 1 hour.

FIG. 3A shows the results of confirming the cell division-promoting effects of Muller glia by reducing external Prox1 in the retina of damaged mice, and shows the results simultaneously showing the distribution of Muller glia and Prox1 proteins expressing EGFP and Sox2 in retinal tissues of Prox1 (fg/fg) normal mice with retinal damage and Prox1 (fg/fg); Chx10-CreER mice in which Prox1 is removed in a bipolar cell-specific manner and EGFP is alternatively expressed.

FIG. 3B shows the results of showing EGFP, Muller glia (Sox2) and neoplastic cells (EdU) in the central and peripheral parts of the retinal tissue of each mouse, which is the same as in FIG. 3A.

FIG. 3C shows the results of showing the distribution of microglia labeled with Iba1 in each mouse retina, which is the same as in FIG. 3B.

MODES OF THE INVENTION

Figure 1A:
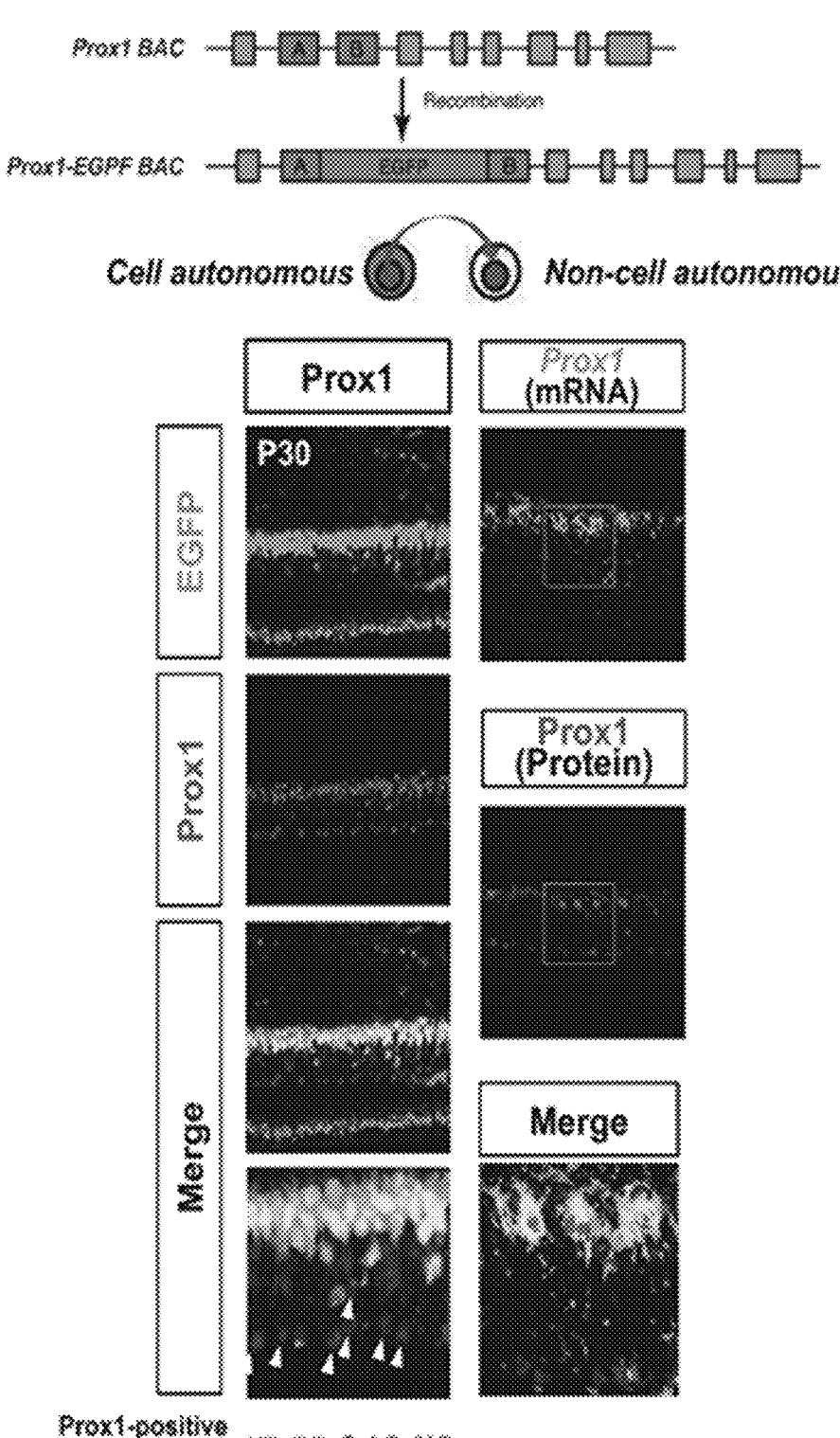
FIG. 1B shows the results of EGFP expression instead of specifically removing the Prox1 gene from mouse Muller glia using the Cre-loxP system, means that the Prox1 gene has been removed from Muller glia labeled with R26-tdTomato by expressing R26-tdTomato red fluorescent protein in cells subjected to genetic recombination using R26-tdTomato transgenic mice, and shows the results of confirming that the Prox1 protein shown in these cells is derived from the outside.

The present inventors have discovered external Prox1 in Muller glia as a target capable of treating a disease caused by retinal damage or degeneration in mammals, and confirmed therapeutic potential by suppressing the influx of external Prox1, thereby completing the present invention based on this.

Thus, the present invention provides a pharmaceutical composition for preventing or treating a retinal neurodegenerative disease, comprising a prospero homeobox 1 (Prox1) inhibitor as an active ingredient.

In the present invention, a Prox1 protein encoded by the Prox1 gene comprises a homeobox domain including a 60-amino acid helix-turn-helix structure that binds to DNA and RNA as a type of homeoprotein. The protein is conserved in vertebrates and is known to play various roles in the development of the liver, retina, lymphatic system, and the like. In particular, it has been reported to have all the functions of regulating proliferation of cells, allowing cells to migrate to an appropriate position, and differentiating the cells such that the cells have unique functions. Further, changes in the level of the protein have been reported in cancers that occur in tissues such as the colon, brain, blood, breast, pancreas, liver and esophagus. The Prox1 protein is expressed in retinal neurons in the mammalian retina, and it is known that Prox1 is present in a very small amount in Muller glia.

In the present invention, the Prox1 gene may include a base sequence represented by SEQ ID NO: 1 or 3. In this case, it is possible to include a base sequence having a sequence homology of 70% or more, preferably 80% or more, more preferably 90% or more, and most preferably 95, 96, 97, 98, 99% or more with the base sequence represented by SEQ ID NO: 1 or 3.

In the present invention, the Prox1 protein includes a Prox1 protein including an amino acid sequence represented by SEQ ID NO: 2 or 4 and a functional equivalent of the protein. The "functional equivalent" refers to a protein which has a sequence homology of at least 70% or more, preferably 80% or more, more preferably 90% or more, and even more preferably 95, 96, 97, 98, 99% or more with the amino acid sequence represented by SEQ ID NO: 2 or 4 as a result of addition, substitution or deletion of an amino acid, and exhibits substantially the same physiological activity as that of a protein represented by SEQ ID NO: 2 or 4. The "substantially the same physiological activity" refers to activity in the mammalian retina.

In the present invention, the Muller glia are a type of retinal glia cell first discovered by Heinrich Muller, and are the most common type of glia cell in the retina of a vertebrate as sustentacular cells for a neuron like other neuroglia. The cell body of Muller glia is located in the inner nuclear layer of the retina, but spans the entire retina. Muller glia maintain the structural and functional stability of retinal cells, and are specifically known to perform a role such as neurotransmitter absorption, cell debris removal, $K^+$ level regulation, glycogen storage, and mechanical support of receptors and retinal nerves. In lower vertebrates such as fish such as zebrafish, amphibians, and reptiles, it is known that when the retina is damaged, Muller glia in the same retina can regenerate damaged retinal neurons while being converted into retinal neuronal progenitor cells to proliferate and differentiate into new retinal cells. However, it is known that regeneration of retinal neurons does not occur in the mammalian retina because the cell division of Muller glia is suppressed.

However, the present inventors confirmed through the specific embodiments below that when suppressing the migration and accumulation of Prox1 from the mammalian retinal neurons to Muller glia during retinal damage, the regeneration process of retinal neurons could be induced by promoting the division of Muller glia. In addition, it was confirmed that when the migration and accumulation of Prox1 to Muller glia are suppressed, the effect could be exhibited by suppressing the proliferation of microglia that induce phagocytosis and inflammatory responses.

Specifically, in an embodiment of the present invention, as a result of analyzing the expression pattern of the Prox1 protein in the retina, it was confirmed that the Prox1 protein is present in horizontal cells, bipolar cells, amacrine cells and Muller glia, and in particular, it was confirmed for the first time that the Prox1 protein in Muller glia was not expressed inside Muller glia but was introduced from the outside (see Example 1).

In another embodiment of the present invention, as a result of analyzing whether changes in the level of the Prox1 protein in the retina occur during retinal damage due to various causes in mammals, a rapid increase in the Prox1 protein was observed only in Muller glia without any change in horizontal cells, bipolar cells and amacrine cells (see Examples 2-1 and 2-2).

In still another embodiment of the present invention, as a result of selectively removing the expression of the Prox1 gene in bipolar cells, which are retinal neurons adjacent to Muller glia, since it was confirmed that the level of the Prox1 protein was reduced in Muller glia in the damaged retina, it could be confirmed again that Prox1 in Muller glia was expressed in retinal neurons including bipolar cells and introduced. Furthermore, it was found that in such cases, the cell division of Muller glia is promoted in the damaged retina. Through this, it could be seen that a significant portion of the Prox1 protein in Muller glia was derived from bipolar cells, and a decrease in the expression of the Prox1 gene in bipolar cells induced the division of Muller glia during retinal damage through a series of processes of reducing Prox1 in Muller glia and the resulting decrease in amount of Prox1 secretion and leading to the decrease in Prox1 migrating to the Muller glia. Further, it was confirmed that the proliferation of microglia that induce phagocytosis and inflammatory responses is suppressed under the same conditions. Therefore, it could be seen that Prox1 in Muller glia also serves to promote the proliferation of microglia in the retina (see Example 3).

In yet another embodiment of the present invention, as a result of administering a Prox1-neutralizing antibody to suppress the migration of Prox1 to Muller glia after retinal damage, it was confirmed that the level of Prox1 in Muller glia was not increased. Through this, it was confirmed that suppression of Prox1 protein migration to Muller glia through intraocular injection of the Prox1-neutralizing antibody induced division of Muller glia, and thus could induce nerve regeneration by differentiation of Muller glia into retinal neurons in the future (see Example 4).

In the present invention, the inhibitor includes both an inhibitor which suppresses the expression of the Prox1 gene in retinal neurons and an inhibitor which suppresses the migration of the Prox1 protein from retinal neurons to Muller glia.

As used herein, an expression inhibitor which suppresses the expression of the Prox1 gene refers to an expression inhibitor which causes a decrease in the expression of a target gene protein. In the present invention, the expression inhibitor includes an expression inhibitor which suppresses the expression of the Prox1 protein in retinal neurons around Muller glia, preferably, bipolar cells, and may be specifically any one selected from the group consisting of an antisense nucleotide that complementarily binds to mRNA of the Prox1 gene, small interfering RNA (siRNA), short hairpin RNA (shRNA), a ribozyme and CRISPR/Cas9, but is not limited thereto.

In the present invention, the inhibitor which suppresses the migration of the Prox1 protein may be specifically any one selected from the group consisting of antibodies, peptides, peptide analogues, aptamers and compounds, which specifically bind to the Prox1 protein or competitively suppress the binding of Prox1 and the Muller glia cell membrane and may be preferably an antibody, but is not limited thereto.

In the present invention, the antibody is not limited to, but may be typically a polyclonal antibody including different antibodies directed against different epitopes (antigen determinants) or a monoclonal antibody directed against a single determinant on an antigen, and may be more specifically a rabbit polyclonal antibody (Cat #ABN278) manufactured by Millipore or a mouse monoclonal antibody (Cat #SC81983) manufactured by Santacruz.

As used herein, the term "prevention" refers to all actions that suppress a retinal neurodegenerative disease or delay the onset of the retinal neurodegenerative disease by administering the pharmaceutical composition according to the present invention.

As used herein, the term "treatment" refers to all actions that ameliorate or beneficially change symptoms caused by a retinal neurodegenerative disease by administering the pharmaceutical composition according to the present invention.

In the present invention, the retinal neurodegenerative disease includes related diseases that are caused by damage or degeneration of a retinal nerve and may be treated by regeneration of the retinal nerve. Preferably, the retinal neurodegenerative disease may be any one selected from the group consisting of retinitis pigmentosa, Leber congenital amaurosis (LCA), retinal detachment, macular degeneration, diabetic retinopathy, glaucoma, central serous retinopathy and senile retinal degeneration, but is not limited thereto.

The pharmaceutical composition according to the present invention may be used alone or in combination with surgery, radiotherapy, chemotherapy and a biological response regulator for the treatment of a retinal neurodegenerative disease, and may be preferably used in combination with a drug that promotes the differentiation of nerve cells.

In addition, the present invention provides a pharmaceutical preparation for preventing or treating a retinal neurodegenerative disease, comprising the pharmaceutical composition.

The pharmaceutical composition according to the present invention includes a Prox1 migration inhibitor as an active ingredient, and may further include a pharmaceutically acceptable carrier. The pharmaceutically acceptable carrier is typically used in formulation, and includes saline, sterile water, Ringer's solution, buffered saline, cyclodextrin, a dextrose solution, a maltodextrin solution, glycerol, ethanol, liposomes, and the like, but is not limited thereto, and may further include other typical additives such as an antioxidant and a buffer, if necessary. Furthermore, the pharmaceutically acceptable carrier may be formulated into an injectable formulation, such as an aqueous solution, a suspension, and an emulsion, an infusion such as an infusion bag, a spray such as an aerosol preparation, a pill, a capsule, a granule, or a tablet by additionally adding a diluent, a dispersant, a surfactant, a binder, a lubricant, and the like. With regard to suitable pharmaceutically acceptable carriers and formulations, the composition may be preferably formulated according to each ingredient by using the methods disclosed in Remington's reference. The pharmaceutical composition of the present invention is not particularly limited in formulation, but may be formulated into an injection, an infusion, a spray formulation, a liquid formulation, an external preparation for skin, or the like.

The pharmaceutical composition of the present invention may be orally administered or may be parenterally administered (for example, applied intravenously, subcutaneously, intraperitoneally, or locally including the eyeball), and the administration dose may vary depending on a patient's condition and body weight, severity of disease, drug form, and administration route and period according to the target method, but the administration dose may be properly selected by those skilled in the art.

The pharmaceutical composition of the present invention is administered in a pharmaceutically effective amount. As used herein, the "pharmaceutically effective amount" refers to an amount sufficient for treating or diagnosing a disease at a reasonable benefit/risk ratio applicable to medical treatment or diagnosis, and an effective dosage level may be determined according to factors including the type of disease of patients, the severity of disease, the activity of drugs, sensitivity to drugs, administration time, administration route, excretion rate, treatment period, and simultaneously used drugs, and other factors well known in the medical field. The pharmaceutical composition according to the present invention may be administered as an individual therapeutic agent or in combination with other therapeutic agents, may be administered sequentially or simultaneously with therapeutic agents in the related art, and may be administered in a single dose or multiple doses. It is important to administer the composition in a minimum amount that can obtain the maximum effect without any side effects, in consideration of all the aforementioned factors, and this amount may be easily determined by those skilled in the art.

Specifically, an effective amount of the pharmaceutical composition of the present invention may vary depending on the age, sex, condition, and body weight of a patient, the absorption of the active ingredient in the body, inactivation rate and excretion rate, disease type, and the drugs used in combination, and in general, 0.001 to 150 mg, preferably 0.001 to 100 mg of the pharmaceutical composition of the present invention per 1 kg of a body weight may be administered daily or every other day or may be dividedly administered once to three times a day. However, since the effective amount may be increased or decreased depending on the administration route, the severity of obesity, gender, body weight, age, and the like, the dosage is not intended to limit the scope of the present invention in any way.

As another aspect of the present invention, the present invention provides a method for preventing or treating a retinal neurodegenerative disease, the method comprising administering the pharmaceutical composition to an individual.

As used herein, the "individual" refers to a subject in need of treatment of a disease, and more specifically, refers to a mammal such as a human or a non-human primate, a mouse, a rat, a dog, a cat, a horse, and a cow.

Further, the present invention provides a use of the pharmaceutical composition for preventing or treating a retinal neurodegenerative disease.

Hereinafter, preferred examples for helping the understanding of the present invention will be suggested. However, the following examples are provided only to more easily understand the present invention, and the contents of the present invention are not limited by the following examples.

EXAMPLES

Example 1. Experimental Materials and Experimental Methods

Production of Transgenic Mice

Prox1::EGFP BAC TG mouse, STOCK Tg (Prox1-EGFP) KY221Gsat/Mmucd (Prox1::EGFP) was obtained from MMRRC.

Prox1$^{f/g}$, Chx10-CreER$^{r2}$ and Glast-CreER$^{r2}$ mice were obtained from RIKEN CDB(Prox1$^{f/g}$), RIKEN BRC(Chx10-CreER$^{r2}$), and Johns Hopkins University (Glast-CreER$^{r2}$), respectively. These mice were maintained and bred in a mouse facility free of specific pathogens. Prox1$^{f/g}$ mice were mated with MG cell-specific Glast-CreER$^{r2}$ mice or BP cell-specific Chx10-CreER$^{r2}$ mice to obtain mice that are Prox1-deficient in Muller glia (MG) or bipolar cells (BPs). In these mice, repeated intraperitoneal administration of tamoxifen (Tam) (75 mg/kg) activates CreER$^{r2}$ recombinase in Glast-positive MG or Chx10-positive BPs, and subsequently induces the deletion of MG cell-specific or BP cell-specific Prox1 and the expression of complementary EGFP.

Meanwhile, all animal experiments conducted in these examples were conducted in accordance with a protocol approved by the Institutional Animal Care and Use Committee (IACUC) of the Korea Advanced Institute of Science and Technology (KAIST).

Immunohistochemistry

Frozen mouse eye tissue sections (20 µm) were cultured in a blocking solution (PBS containing 10% donkey serum and 0.1% Triton X-100) at room temperature for 1 hour. Next, the tissue sections were treated with a blocking solution containing a primary antibody, which was not supplemented with Triton X-100, and cultured at 4° C. for 16 hours. Subsequently, the tissue sections were treated with a fluorophore-conjugated secondary antibody, and then cultured, and then a fluorescence signal of the tissue section was observed and analyzed under an Olympus FV1000 confocal microscope.

In Situ Hybridization

Sense and antisense RNA probes were prepared by T7 and SP6 RNA polymerases using a full-length cDNA of mouse Prox1 in a pGEM-T vector. In the mouse retinal tissue sections, ISH of Prox1 mRNA was performed with an RNA probe labeled with digoxigenin (DIG). Subsequently, the tissue sections were co-stained with an anti-DIG Fab fragment (Roche) conjugated with a rabbit anti-Prox1 antibody and an alkaline phosphatase (AP) which detects a DIG-labeled probe. An anti-DIG Fab fragment bound to the DIG-labeled RNA probe was stained with a secondary antibody labeled with a fluorophore which detects an anti-Prox1 antibody and then visualized by an HNPP fluorescence detection set (Roche). Subsequently, a fluorescence image of an ISH signal was obtained under an Olympus FV1000 confocal microscope.

Example 1. Confirmation of Presence of External Prox1 Protein in Muller Glia The present inventors sought to investigate the expression pattern of the Prox1 gene in the mouse retina, and used transgenic mice in which an enhanced green fluorescent protein (EGFP) was inserted into the Prox1 gene site as shown in FIG. 1A for this purpose. Through this, EGFP fluorescence can be observed and simultaneously, the distribution of the Prox1 protein produced by the expression of the Prox1 gene can be confirmed. Thus, as a result of investigating the expression pattern of the Prox1 protein in cells present in the retina, theoretically, the Prox1 protein (shown in red) should be detected only in cells in which EGFP fluorescence is observed as can be seen in FIG. 1A, that is, horizontal cells (HZs) and bipolar cells (BPs), but a peculiar phenomenon, in which the Prox1 protein was also observed in cells in which EGFP fluorescence was not observed, that is, amacrine cells (ACs) and Muller glia (MG), occurred.

Therefore, although EGFP fluorescence was not observed in Muller glia cells, in order to investigate the Prox1 protein in the Muller glia, the present inventors performed a gene manipulation method which selectively destroys the Prox1 gene in Muller glia using the Cre-loxP system as illustrated in FIG. 1B. Specifically, transgenic mice were produced by the method described in Experimental Example 1-1 such that EGFP was expressed instead of a site where the Prox1 gene disappeared, and in this case, since Prox1 is selectively removed from Muller glia by the action of Glast-CreER, which shows activity by an estrogen analogue tamoxifen (Tam), EGFP fluorescence appears only in Muller glia. Further, cells subjected to genetic recombination with a Cre recombinant enzyme along with EGFP fluorescence labeling could also be labeled with R26-tdTomato red fluorescent protein to confirm whether the gene was expressed at a Prox1 gene site by green fluorescence and whether the Prox1 gene was removed by red fluorescence. That is, as can be seen in the schematic view of FIG. 1B, when the expression occurs at the corresponding site after the removal of the Prox1 gene, the corresponding cells express both green and red to display yellow fluorescence, and when the Prox1 gene is only removed without any expression at the Prox1 gene site, red fluorescence is seen.

As a result of the experiment, only red fluorescence was observed in Muller glia, and through this, it could be seen that Muller glia expresses the Prox1 protein without any expression of the Prox1 gene site. In other words, it was confirmed that the Prox1 protein present in Muller glia was not expressed in Muller glia, but was introduced from the outside.

Example 2. Confirmation of Accumulation of Prox1 Protein in Muller Glia of Damaged Mouse Retina 2-1. Confirmation of Prox1 Protein Accumulation by MNU Treatment Based on the results of Example 1 above, the present inventors performed an experiment to investigate whether a change in the level of the Prox1 protein is induced in Muller glia when the retina is damaged. Specifically, as illustrated in FIG. 2A, an analysis was performed by injecting a vehicle (PBS containing 0.05% acetic acid) or a DNA-damaging factor N-methyl-N-nitrosourea (MNU) (60 mg/kg in the vehicle) into mice to selectively degenerate photoreceptor cells (PRs) in the retina of adult mice and performing immunohistochemistry in the same manner as in Experimental Example 1-2 using eyeball tissue sections of mice every day until day 7 after injection. In this case, apoptotic cells were labeled with TUNEL, and newly generated cells were labeled with EdU.

As a result of the analysis, as illustrated in FIG. 2B, the newly generated cells were found to be microglia which were introduced from outside the eyeball to remove apoptotic cells, as is well known in mammals. In addition, as shown in FIG. 2C, it was confirmed that the expression level of the Prox1 protein was increased in Muller glia (Sox2+) indicated by the expression of Sox2 protein in the retina of mice degenerating after exposure to MNU. Furthermore, from these results, as seen in FIG. 2D, it could be seen that an increase in Prox1 was concentrated only in Muller glia without any change in other cells in the retina, that is, bipolar cells (BP) and amacrine cells (AC). In contrast, as shown in FIG. 2E, a change in amount of the Prox1 protein in Muller glia indicated by Gfap-EGFP in the zebrafish retina, which is capable of nerve regeneration upon retinal damage was not observed even after degeneration of photoreceptor cells by MNU.

That is, through the results, it was predicted that in the mammalian retina, Prox1 in Muller glia plays a role in preventing retinal nerve regeneration by suppressing the division of Muller glia and inducing the proliferation of microglia. Therefore, the present inventors predicted that when the accumulation of the Prox1 protein does not occur in Muller glia as in the case of zebrafish, Muller glia can differentiate into neurons after cell division to regenerate nerves.

2-2. Confirmation of Prox1 Protein Accumulation in NMDA, Light-Treated and Retinal Degenerative Disease Model Mice The accumulation of the Prox1 protein was confirmed in the retina damaged by various factors using the same method as the method of confirming the accumulation of the Prox1 protein in Example 2-1.

The apoptosis of retinal ganglion cells (GCs) and amacrine cells (ACs) was induced by injecting a vehicle (PBS) or N-methyl-D-aspartic acid (NMDA) into the eyeballs of mice. NMDA was diluted to a concentration of 20 mM with sterile PBS, and then 1 ul of the NMDA/PBS solution was loaded into a Hamilton syringe equipped with a blunt 33-gauge needle and injected into the vitreal space of the mouse eyes. After 7 days, mouse eyeballs were removed and the Prox1 level in Muller glia cells labeled with Sox2 was investigated by immunohistochemistry. As a result, as shown in FIG. 2F, it was confirmed that the expression level of the Prox1 protein in Muller glia (Sox2+) indicated by the expression of the Sox2 protein increased. Further, it could be seen that an increase in Prox1 was concentrated only in Muller glia without any change in other cells in the retina, that is, bipolar cells (BP) and amacrine cells (AC).

Mice were bred while being exposed to very strong light of 100,000 Lux for 1 hour to induce damage to retinal photoreceptor cells (PRs). After 7 days, mouse eyeballs were removed and the Prox1 level in Muller glia cells labeled with Sox2 was investigated by immunohistochemistry. As a result, as shown in FIG. 2G, it was confirmed that the expression level of the Prox1 protein in Muller glia (Sox2+) indicated by the expression of the Sox2 protein increased. Further, it could be seen that an increase in Prox1 was concentrated only in Muller glia without any change in other cells in the retina, that is, bipolar cells (BP) and amacrine cells (AC).

Figure 2H:
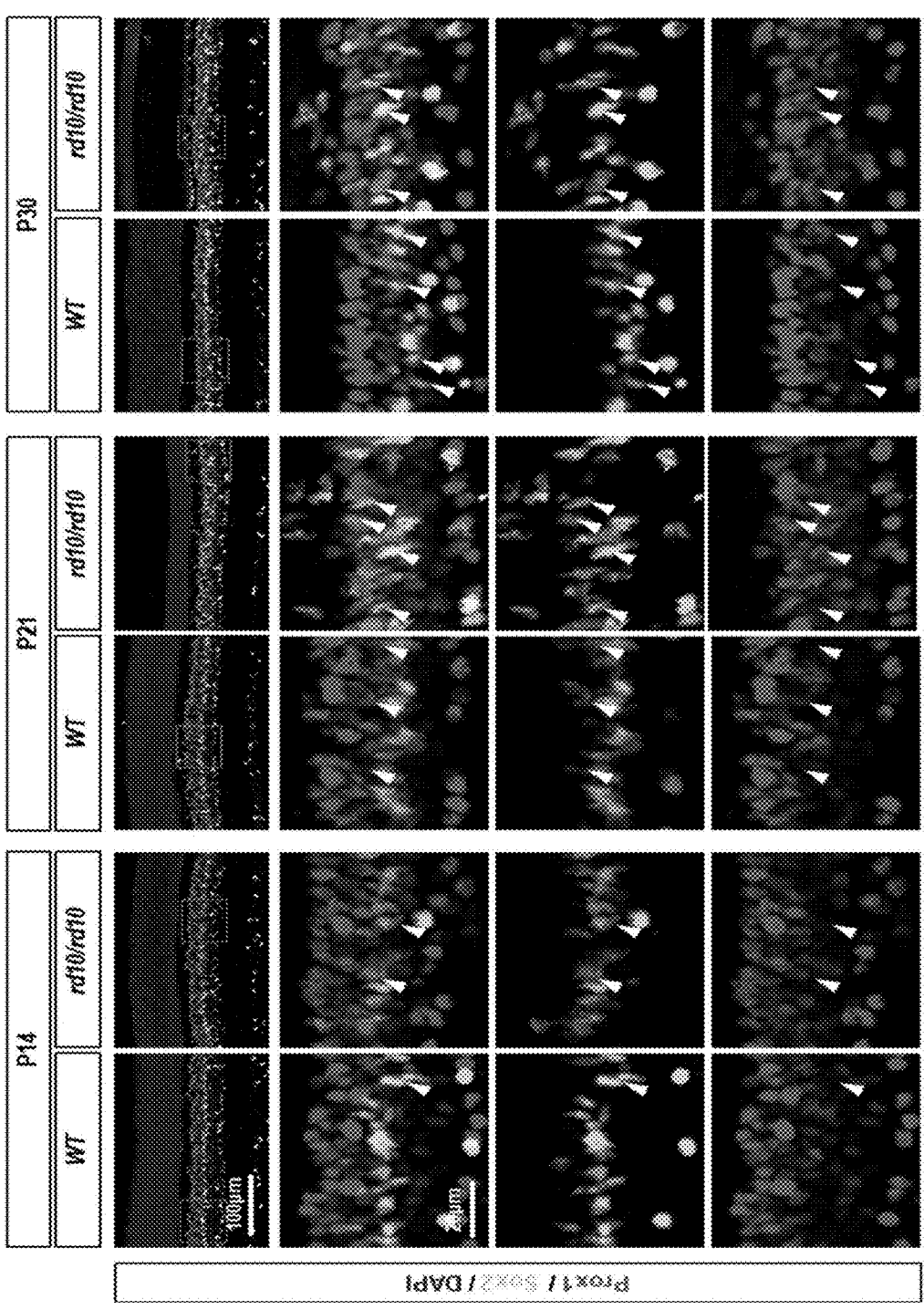
FIG. 2H shows the results of confirming the distribution of Prox1 in Muller glia cells of Rd10 mice, which are a congenital retinal degenerative disease model.

Prox1 levels in Muller glia cells labeled with Sox2 were examined by immunohistochemistry by removing the eyeballs of rd10 mice, which are an animal model of a retinal neurodegenerative disease in which photoreceptor cells (PRs) are congenitally degenerated, on day 14 after birth, day 21 after birth and day 30 after birth, when the photoreceptor cells were considered to be completely damaged. As a result, as shown in FIG. 2H, it was confirmed that the expression level of the Prox1 protein in Muller glia (Sox2+) indicated by the expression of the Sox2 protein increased. Further, it could be seen that an increase in Prox1 was concentrated only in Muller glia without any change in other cells in the retina, that is, bipolar cells (BP) and amacrine cells (AC).

Figure 2I:
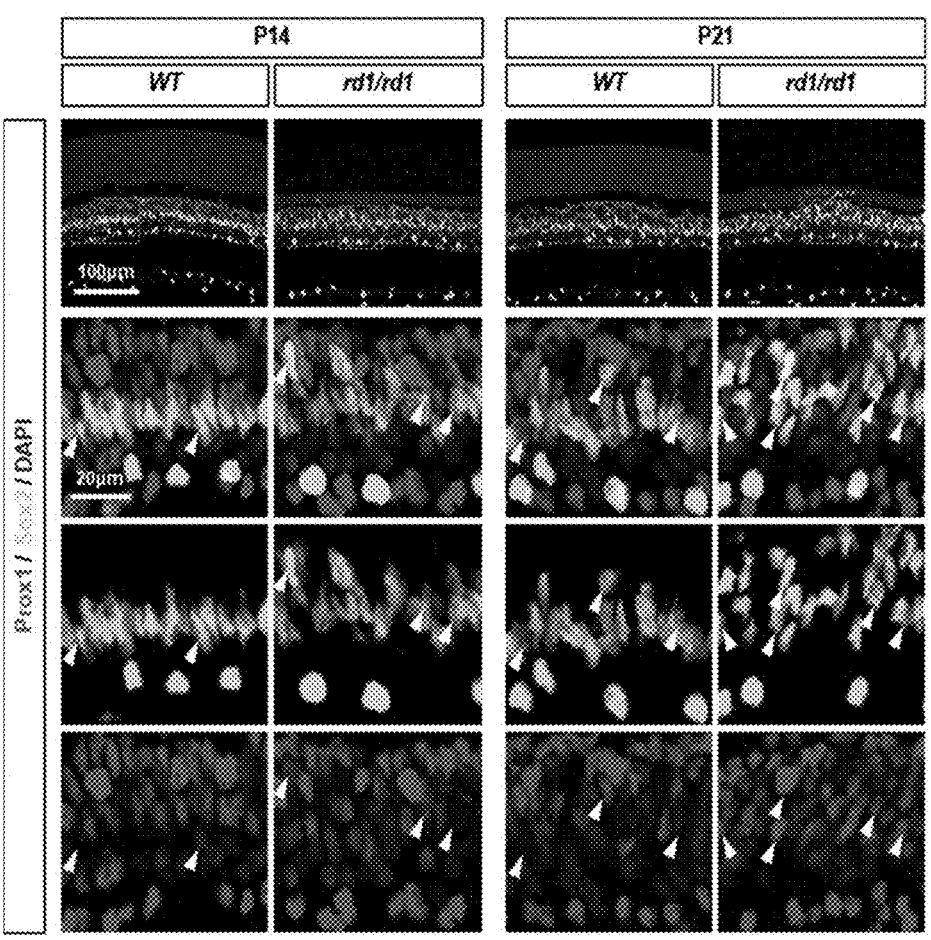
FIG. 2I shows the results of confirming the distribution of Prox1 in Muller glia cells of Rd1 mice, which are a congenital retinal degenerative disease model.

Prox1 levels in Muller glia cells labeled with Sox2 were examined by immunohistochemistry by removing the eyeballs of rd10 mice, in which the progression of congenital degeneration of photoreceptor cells (PRs) occurs faster than in the aforementioned rd10 mice, on day 14 after birth and day 21 after birth, when the photoreceptor cells were considered to be completely damaged. As a result, as shown in FIG. 2I, it was confirmed that the expression level of the Prox1 protein in Muller glia (Sox2+) indicated by the expression of the Sox2 protein increased. Further, it could be seen that an increase in Prox1 was concentrated only in Muller glia without any change in other cells in the retina, that is, bipolar cells (BP) and amacrine cells (AC).

Example 3. Confirmation of Promotion of Cell Division of Muller Glia by Reduction of External Prox1 in Damaged Mouse Retina The present inventors confirmed that Prox1 in Muller glia was introduced from the outside in Examples 2-1 and 2-2, and thus predicted that external Prox1 in Muller glia was derived from retinal neurons adjacent to Muller glia. Therefore, in order to confirm this experimentally, as shown in FIG. 3A, the Prox1 gene was selectively removed from bipolar cells using Chx10-CreER, and genes of cells from which Prox1 had been removed were modified such that EGFP was expressed instead. As a result, unlike normal Prox1 (fg/fg) mice with retinal damage, the amount of Prox1 was decreased not only in bipolar cells in which Prox1 had been removed and in which EGFP was expressed instead, but also in Muller glia in which there is no EGFP. These results mean that a significant portion of Prox1 in Muller glia is derived from bipolar cells.

In addition, as can be seen in FIGS. 3B and 3C, in the damaged retina of normal mice, EdU indicating cell division appeared in microglia labeled with Iba1 without appearing in Muller glia labeled with Sox2, whereas in the retina of Prox1 (fg/fg); Chx10-CreER mice whose expression was reduced by removing the Prox1 gene, newly generated cells labeled with EdU were found to be Muller glia labeled with Sox2. These results mean that Muller glia are divided according to a decrease in Prox1 in Muller glia during retinal damage, and means that Prox1 in Muller glia serves to promote the proliferation of microglia.

Example 4. Confirmation of Suppression of Prox1 Migration Using Neutralizing Antibody Based on the results of the above examples, the present inventors used a neutralizing antibody against Prox1 to substantially suppress the migration of Prox1 to Muller glia in the mouse eyeball. Two commercially available antibodies (Cat #ABN278 Rabbit polyclonal antibody (Millipore) and Cat #SC81983 Mouse monoclonal antibody (Santa Cruz)) were used as Prox1-neutralizing antibodies for the experiment.

More specifically, the retina was damaged by injecting MNU into mice, and one day later, a non-immunized mouse antibody (mIgG, 50 ng) or a Prox1-neutralizing antibody (α-Prox1, 50 ng) was injected into the mouse eyeball. In this case, the antibody was diluted with sterile PBS, 1 μl (50 ng) of the antibody/PBS solution was loaded into a Hamilton syringe equipped with a blunt 33-gauge needle and injected into the vitreal space of the mouse eyes. After 3 days, mouse eyeballs were removed and the Prox1 level in Muller glia or Muller glia-derived cells labeled with tdTomato was investigated by immunohistochemistry.

Figure 4:
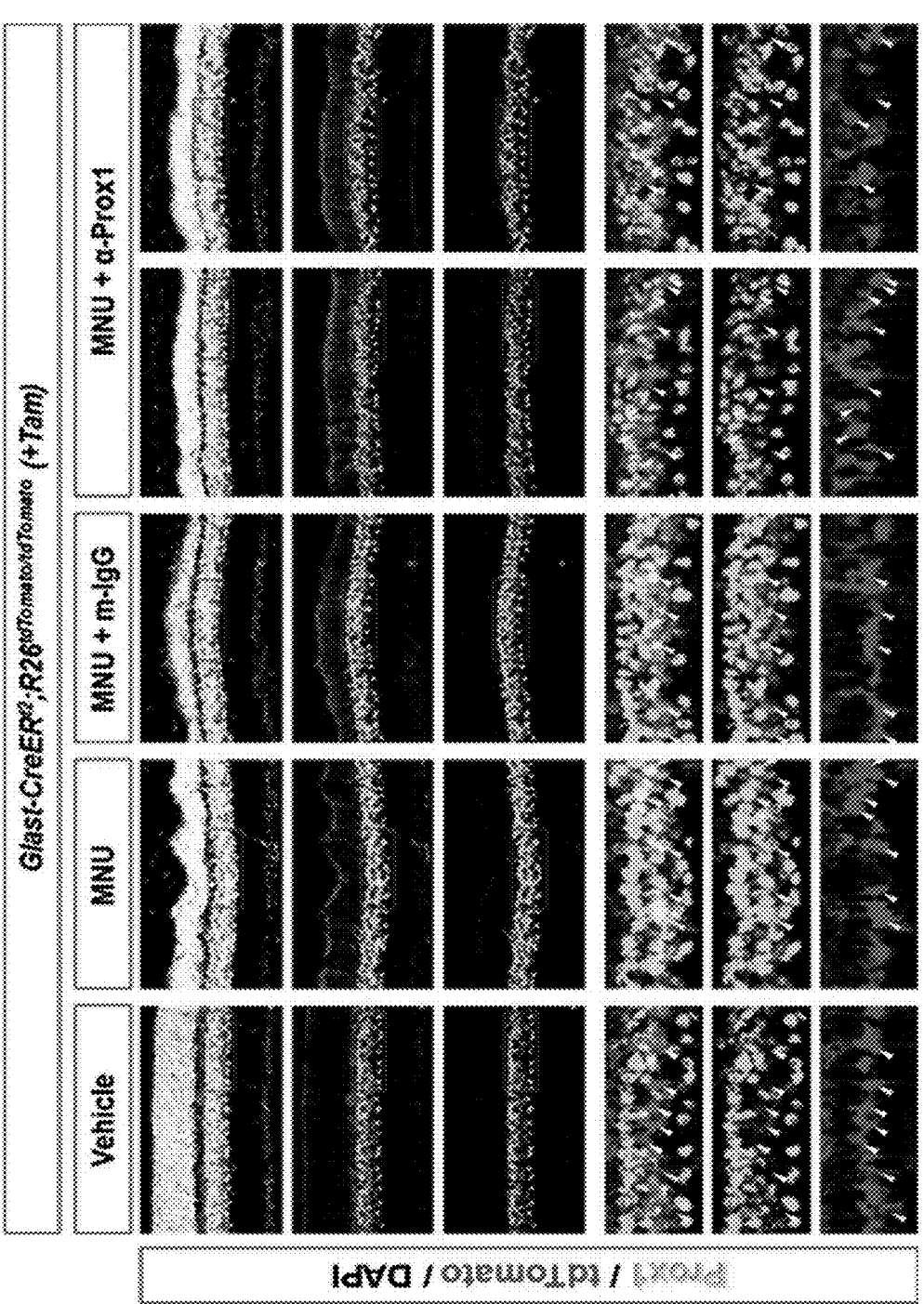
FIG. 4 shows the results of showing the level of Prox1 protein in Muller glia of ocular tissue intravitreally administered a non-immunized mouse antibody or a Prox1-neutralizing mouse monoclonal antibody, respectively, after damaging the retina by injecting MNU into mice.

As a result, as shown in FIG. 4, the Prox1 level was not increased even after the damage by MNU in the Muller glia-derived cells of the eyeball injected with the Prox1-neutralizing antibody. This means that the migration of the Prox1 protein to Muller glia can be suppressed by injecting a Prox1-neutralizing antibody into the eyeball. In addition, as confirmed in Example 3, based on the fact that the division of Muller glia is induced only when the amount of Prox1 in Muller glia is reduced, the grounds that the Prox1-neutralizing antibody can be used to induce the division of Muller glia in the mammalian retina have been established. Furthermore, simultaneous injection of various neuronal differentiation-promoting drugs along with the Prox1-neutralizing antibody can induce the regeneration of new retinal neurons to replace damaged retinal neurons.

The above-described description of the present invention is provided for illustrative purposes, and those skilled in the art to which the present invention pertains will understand that the present invention can be easily modified into other specific forms without changing the technical spirit or essential features of the present invention. Therefore, it should be understood that the above-described embodiments are only exemplary in all aspects and are not restrictive.

INDUSTRIAL APPLICABILITY

The present invention relates to a pharmaceutical composition for treating various retinal neurodegenerative diseases which cause loss of vision because there is no effective therapeutic method in the related art, and specifically, the inventors of the pharmaceutical composition of the present invention confirmed that Muller glia can be divided by suppressing the accumulation of the Prox1 protein in Muller glia, which occurs during retinal damage. In this aspect, since the pharmaceutical composition comprising the migration inhibitor of Prox1 according to the present invention can induce the regeneration of the damaged retina in mammals, it is expected that the pharmaceutical composition can be widely utilized in the field of treatment of various retinal neurodegenerative diseases causing loss of vision because there is no effective therapeutic method in the related art and in the development of specific retinal regeneration methods.

The invention claimed is:

1. A method for preventing or treating a retinal neurodegenerative disease, the method comprising: administering an effective amount of a neutralizing antibody which specifically binds to and inhibits prospero homeobox 1 (Prox1) to an individual in need thereof.

2. The method of claim 1, wherein the neutralizing antibody suppresses the migration of a Prox1 protein from retinal neurons to Muller glia.

3. The method of claim 1, wherein the retinal neurodegenerative disease is any one selected from the group consisting of retinitis pigmentosa, Leber congenital amaurosis (LCA), retinal detachment, macular degeneration, diabetic retinopathy, glaucoma, central serous retinopathy and senile retinal degeneration.

4. The method of claim 1, wherein the neutralizing antibody which specifically binds to prospero homeobox 1 (Prox1) promotes regeneration of retinal neurons by suppressing the proliferation of microglia which induce phagocytosis and inflammatory responses.

5. The method of claim 1, wherein the neutralizing antibody which specifically binds to prospero homeobox 1 (Prox1) is administered in combination with a neuronal differentiation-promoting drug.

6. The method of claim 1, wherein the neutralizing antibody which specifically binds to prospero homeobox 1 (Prox1) is a pharmaceutical preparation, wherein the pharmaceutical preparation is an injection formulation, an infusion formulation, a spray formulation or a liquid formulation.

7. The method of claim 1, wherein the neutralizing antibody is administered via intraocular administration.

\* \* \* \* \*